(12) United States Patent
Ichimura

(10) Patent No.: US 8,063,200 B2
(45) Date of Patent: Nov. 22, 2011

(54) LABELED COMPOUND AND DETECTION METHOD USING THE SAME

(75) Inventor: Mari Ichimura, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 12/545,654

(22) Filed: Aug. 21, 2009

(65) Prior Publication Data

US 2010/0075321 A1    Mar. 25, 2010

(30) Foreign Application Priority Data

Aug. 25, 2008   (JP) ................. 2008-214868

(51) Int. Cl.
*C07H 19/04* (2006.01)
*C12Q 1/68* (2006.01)
*C07D 215/00* (2006.01)
*C07D 215/38* (2006.01)

(52) U.S. Cl. .......... 536/26.6; 435/6; 546/153; 546/157; 546/159

(58) Field of Classification Search ................. 536/26.6; 546/153, 157, 159; 435/6
See application file for complete search history.

(56) References Cited

U.S. PATENT DOCUMENTS

| | | |
|---|---|---|
| 2003/0149250 A1 | 8/2003 | Kung et al. |
| 2005/0009109 A1 | 1/2005 | Moerner |
| 2005/0158577 A1 | 7/2005 | Ishibashi et al. |

FOREIGN PATENT DOCUMENTS

| | | |
|---|---|---|
| JP | 2000-230132 | 8/2000 |
| JP | 2001-106657 | 4/2001 |
| JP | 2001-106658 | 4/2001 |
| JP | 2001-131128 | 5/2001 |
| JP | 2001-288377 | 10/2001 |
| JP | 2002-226722 | 8/2002 |
| JP | 2004-087463 | 3/2004 |
| JP | 3555736 | 5/2004 |
| JP | 2005-5226 | 1/2005 |
| JP | 2005-035927 | 2/2005 |
| JP | 2005-504055 | 2/2005 |
| JP | 2005-208026 | 8/2005 |
| JP | 2006-124333 | 5/2006 |
| JP | 2006-128437 | 5/2006 |
| JP | 3820752 | 6/2006 |
| JP | 3852517 | 9/2006 |
| JP | 3852518 | 9/2006 |

(Continued)

OTHER PUBLICATIONS

Japanese Office Action for corresponding JP2008-214868 issued on Mar. 23, 2010.

(Continued)

*Primary Examiner* — Jezia Riley
(74) *Attorney, Agent, or Firm* — K&L Gates LLP

(57) ABSTRACT

A labeled compound is so designed that an aromatic tertiary amine compound is bondable with a biomolecule. One of $S^1$ and $S^2$ contains a group bound with a molecular chain 10 (e.g. an oligonucleotide) capable of binding with a biomolecule or a reactive group covalently binding with a reactive group present in the biomolecule, n is 0 or 1, $R^3$ is a phenyl group or a naphthyl group, $Ar^1$ is a phenylene group or a naphthylene group, and $Ar^2$ is any of a phenylene group, a naphthylene group, an anthrylene group, and a phenanthrene group. The detection of a fluorescence emitted by excitation of the labeled compound bound to a biomolecule ensures the biomolecule being detected at high sensitivity and a high SN ratio.

18 Claims, 19 Drawing Sheets

FOREIGN PATENT DOCUMENTS

| | | |
|---|---|---|
| JP | 3852520 | 9/2006 |
| JP | 3852552 | 9/2006 |
| JP | 2006-273737 | 10/2006 |
| JP | 4001118 | 8/2007 |
| WO | 2008/055969 A1 | 5/2008 |

OTHER PUBLICATIONS

Bennie J. Bench, et al., Synthesis and Cellular Effects of Cycloterpenals: Cyclohexadienal-Based Activators of Neurite Outgrowth, Bioorganic & Medicinal Chemistry 16 (2008), pp. 7573-7581, Elsevier.

Richard M. Peck et al., Isocyanates of Dimethylaminostilbenes and Acetylaminofluorene, Jan. 20, 1952, pp. 468-470, vol. 74.

Lingzhi Liu et al., Two-Photon Excitation Fluorescence Resonance Energy Transfer with Small Organic Molecule as Energy Donor for Bioassay, Bioconjugate Chem., 2008, 19, pp. 574-579.

Herbert Meier et al., The Effect of 2,2-Dicyanovinyl Groups as Electron Acceptors in Push-Pull Substituted Oligo (1,4-Phenylenevinylene)s, Tetrahedron Letters 44 (2003), pp. 1915-1918.

Chunying Wu et al., A Novel Fluorescent Probe That Is Brain Permeable and Selectively Binds to Myelin, Journal of Histochemistry & Cytochemistry, 2006, pp. 997-1004, vol. 54(9).

Herbert Meier et al., Bathochromic or Hypsochromic Effects Via the Extension of Conjugation: A Study of Stilbenoid Squaraines, Chem Common, 1999, pp. 977-978.

European Search Report dated Jul. 14, 2010, for corresponding European Appln. No. 0901826.7.

Cremer et al., "Novel Highly Fluorescent Triphenylamine-Based Oligothiophenes", Chem. Mater., Jan. 2007, vol. 19, pp. 4155-4165.

Robinson et al., "The uptake of a fluorescently labelled antisense oligonucleotide in vitro and in vivo", Journal of Neuroscience Methods, 2005, vol. 147, pp. 48-54.

Wu et al., "A Novel Fluorescent Probe that is Brain Permeable and Selectively Binds to Myelin", Journal of Histochemistry and Cytochemistry, 2006, vol. 54, No. 9, pp. 997-1004.

F I G . 2
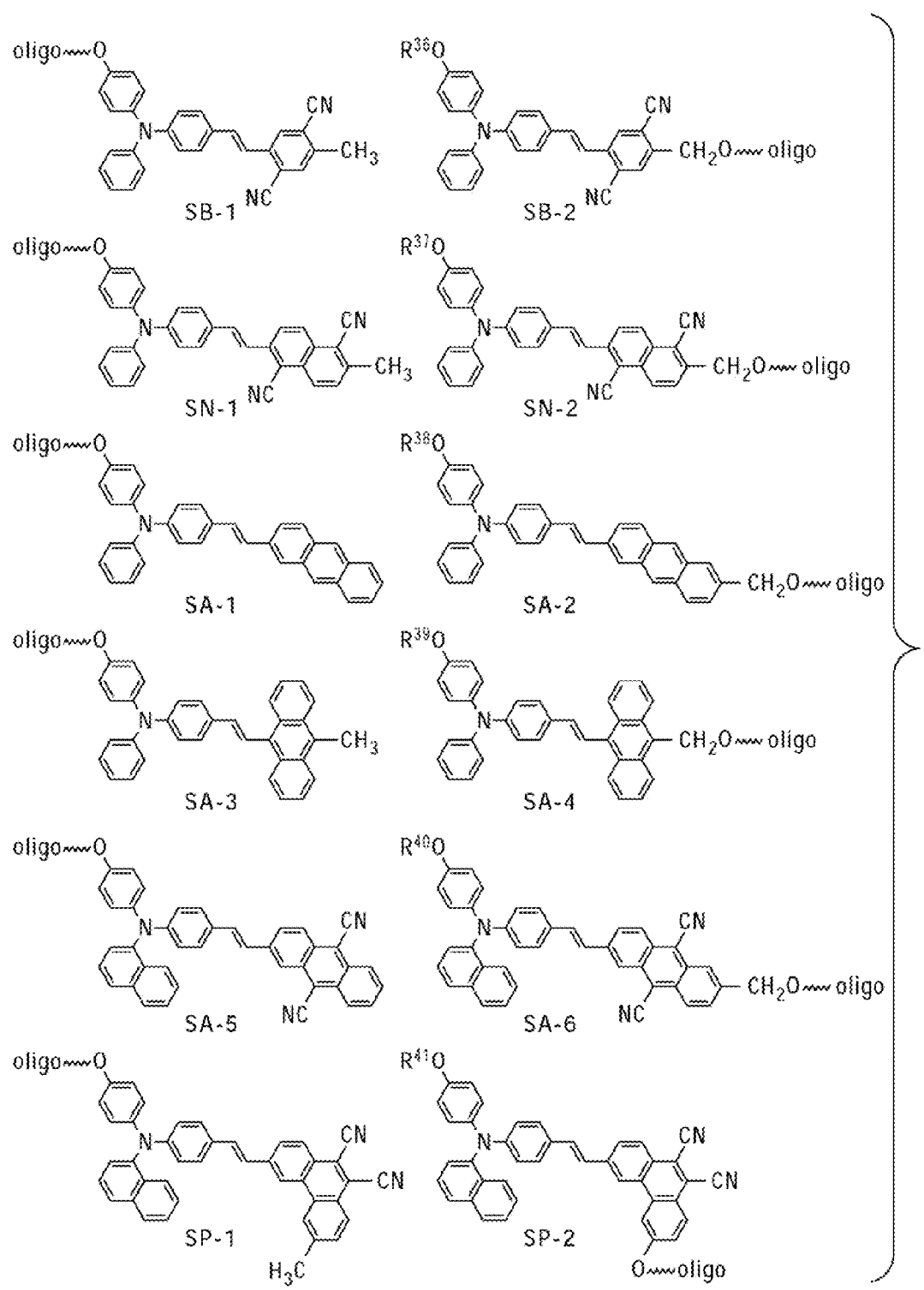

F I G . 1 3 A
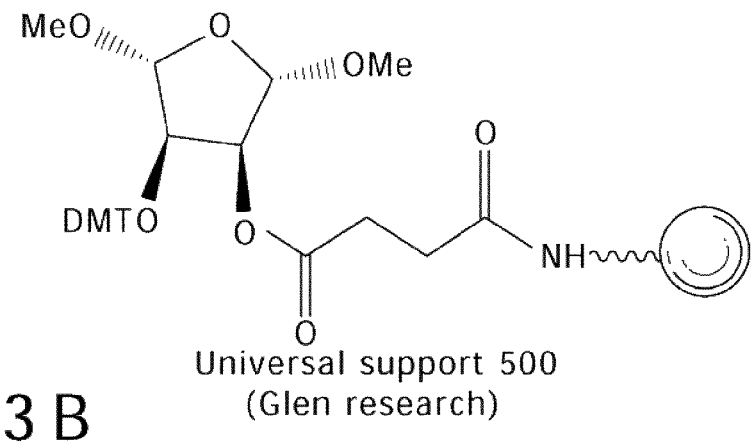
F I G . 1 3 B
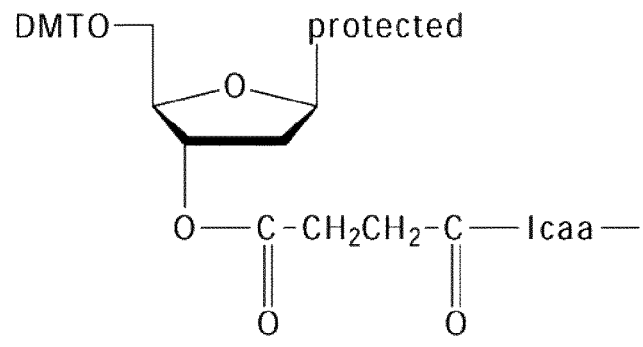
F I G . 1 3 C
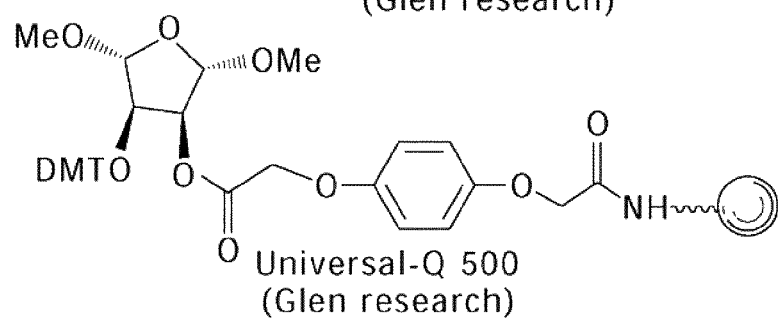
F I G . 1 3 D
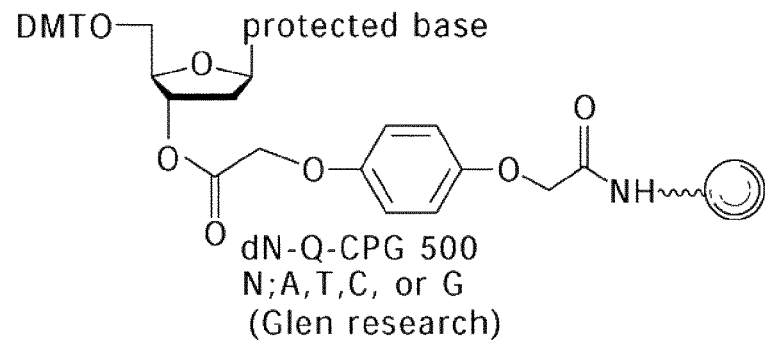

3'-Amino-Modifier C7 CPG
(Glen research)

3'-PT-Amino-Modifier C6 CPG
(Glen research)

5'-Thiol-Modifier C6
(Glen research)

5'-Amino-Modifier C6
(Glen research)

F I G . 16
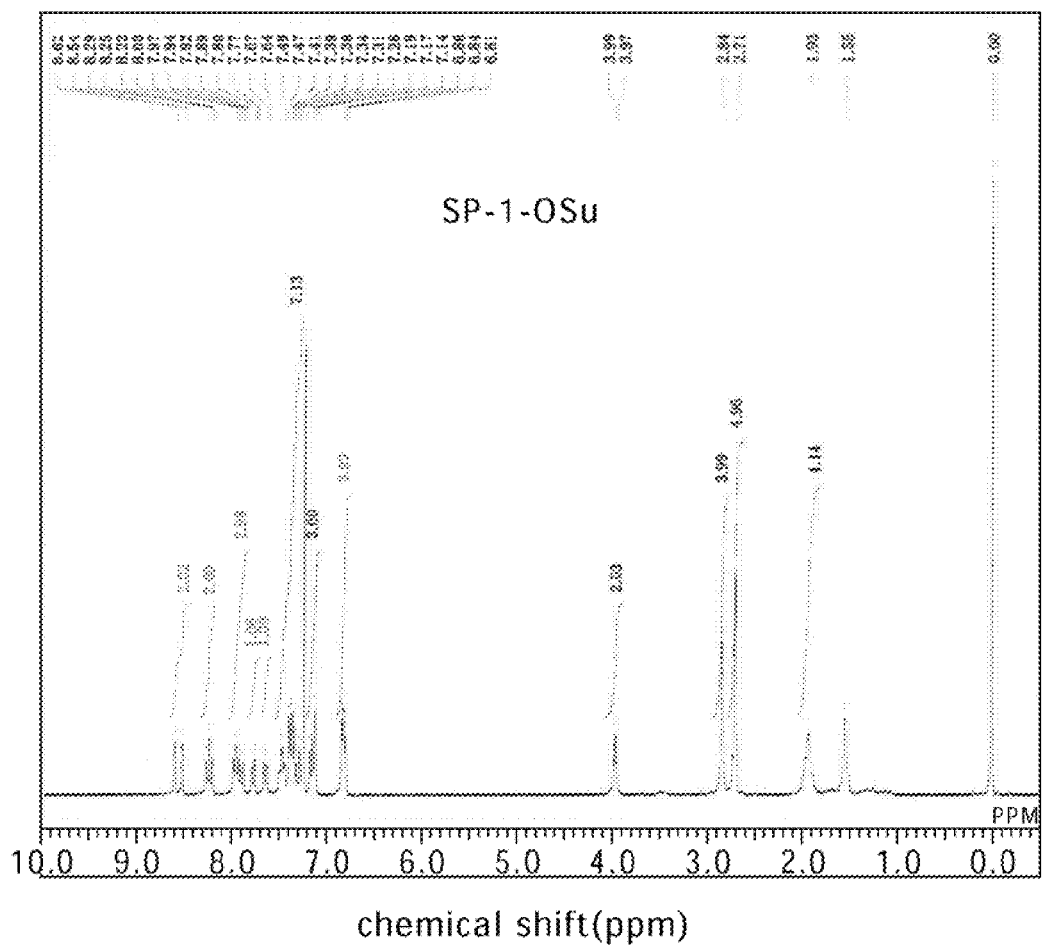
chemical shift(ppm)

LABELED COMPOUND AND DETECTION METHOD USING THE SAME

CROSS REFERENCES TO RELATED APPLICATIONS

The present application claims priority to Japanese Priority Patent Application JP 2008-214868 filed in the Japan Patent Office on Aug. 25, 2008, the entire content of which is hereby incorporated by reference.

BACKGROUND

The present disclosure relates to a labeled compound used for detection of a sample molecule and more particularly, to a labeled compound designed to permit an aromatic tertiary amine compound to be capable of binding with the sample molecule and also to a detection method using the same.

There are known techniques of analyzing biomolecules wherein sample molecules made of various types of biomolecules such as of nucleic acids, proteins, sugars, enzymes, hormones, antigens, antibodies and the like are fluorescently labeled and the fluorescence is detected. This analyzing technique is a fundamental one in the fields of the analysis of life phenomena, genetic diagnosis, tissue engineering and the like and is also an essential one in the screening of medical drugs. For instance, labeling of gene, protein with a fluorescent dye enables a specific type of gene or protein in an analyte to be detected at high sensitivity.

Comprehensive analyses of analytes have been conducted, for example, by labeling many types of oligonucleotides or peptides with fluorescent dyes and using DNA chips or protein chips fixing a microarray of the labeled oligonucleotides or peptides thereon. Moreover, in an immunostaining or molecule imaging technique wherein a specific type of biomolecule such as, for example, of a sugar, protein or the like is labeled with a fluorescent dye and is observed through a fluorescence microscope after generation of a fluorescence, dynamic analyses of an intracellular or intercellular molecule become possible.

The labeled probe obtained by labeling DNA, a DNA base derivative, a DNA oligonucleotide or the like with a fluorescent dye is employed in northern blotting, Southern blotting, in situ hybridization, DNA sequence determination reaction and the like. The antibody or antigen labeled with a fluorescent dye is used for immunoassay making use of an antigen-antibody reaction. There is also known an enzyme immunoassay method to which the avidin (streptoavidin)-biotin linkage is applied and in which avidin modified with a fluorescent dye is used.

For the labeling of a biomolecule serving as a sample to be detected, for example, an aromatic dye compound such as FITC (fluorescein isothiocyanate), TRITC (tetramethylrhodamine isothiocyanate), fluorescein, rhodamine, coumarin, cyanine dye or the like is used as the fluorescent labeling reagent.

Techniques relating to the detection of biomolecules and various types of fluorescent labeling compounds used for the detection of biomolecules are known and reported as shown below.

In Japanese Patent Laid-open No. 2005-208026 (at Paragraphs 0004-0011), entitled "Method of detecting biological molecules, and labeling dye and labeling kit used for the same," (referred to as Patent Document 1) there is the following description.

The method for detecting a biomolecule in the Patent Document 1 is characterized in that a biomolecule sample and an organic EL (electroluminescence) dye are reacted with each other and the fluorescence of the biomolecule sample labeled with the organic EL dye is measured. It is stated that the organic EL dye used is made of a compound containing a conjugated five-membered ring compound, for which there can be used a compound containing at least one hetero atom, selenium atom or boron atom. Moreover, there may be further used a condensed polycyclic compound made of a five-membered ring compound and a conjugated six-membered ring compound, wherein the five-membered ring compound used may be an azole derivative or an imidazole derivative.

Prior to the reaction with a biomolecule, the organic EL dye may be introduced thereinto with any one of functional groups selected from an isocyanate group, an epoxy group, a halogenated alkyl group, a triazine group, a carbodiimide group and an active-esterified carbonyl group.

The labeling dye of the Patent Document 1 is one used for detection of a biomolecule based on fluorescent measurement and is characterized in that it consists of an organic EL dye having a reactive group capable of binding to the biomolecule. It is stated that as the reactive group, there can be used any one of functional groups selected from a carboxylic group, an isocyanate group, an epoxy group, a halogenated alkyl group, a triazine group, a carbodiimide group and an active-esterified carbonyl group.

It is also stated in the Patent Document 1 that the organic EL dye is a compound containing a conjugated five-membered ring compound and a compound containing at least one hetero atom, selenium atom or boron atom may be used as this five-membered ring compound. In addition, there may be further used a condensed polycyclic compound composed of the five-membered ring compound and a conjugated six-membered ring compound. The five-membered ring compound may be an azole derivative or an imidazole derivative.

A variety of organic EL dyes are known aside from those set out in the Patent Document 1. For instance, there have been reported organic EL dyes composed of styryl compounds having a diversity of structures, for example, in Patent Documents indicated below:

Japanese Patent No. 3852517 (paragraphs 0017 to 0020),
Japanese Patent No. 3852518 (paragraphs 0017 to 0020),
Japanese Patent No. 3852520 (paragraphs 0015 to 0018),
Japanese Patent No. 3555736 (paragraphs 0017 to 0020),
Japanese Patent No. 3820752 (paragraphs 0017 to 0020),
Japanese Patent Laid-open No. 2000-230132 (paragraphs 0008 to 0021),
Japanese Patent Laid-open No. 2001-106657 (paragraphs 0008 to 0019),
Japanese Patent Laid-open No. 2001-106658 (paragraphs 0008 to 0012),
Japanese Patent Specification No. 3852552 (paragraphs 0017 to 0037),
Japanese Patent Laid-open No. 2001-131128 (paragraphs 0008 to 0012),
Japanese Patent Laid-open No. 2001-288377 (paragraphs 0007 to 0020),
Japanese Patent Laid-open No. 2002-226722 (paragraphs 0007 to 0014),
Japanese Patent Laid-open No. 2004-87463 (paragraphs 0021 to 0026),
Japanese Patent No. 4001118 (paragraphs 0013 to 0065),
Japanese Patent Laid-open No. 2005-5226 (paragraphs 0013 to 0057),
Japanese Patent Laid-open No. 2005-35927 (paragraphs 0013 to 0042),
Japanese Patent Laid-open No. 2006-124333 (paragraphs 0011 to 0054), Japanese Patent Laid-open No. 2006-128437 (paragraphs 0009 to 0024), and Japanese Patent Laid-open No. 2006-273737 (paragraphs 0009-0027).

SUMMARY

Where the sample molecule labeled with a fluorescent dye, e.g. a biomolecule, is excited with excitation light and the fluorescence emitted from the fluorescent dye is detected with a photodetector to detect the biomolecule, the usual practice is to use a filter that is able to cut off light having wavelengths other than a desired wavelength region and pass a fluorescence within a desired wavelength region to a photodetector in order to intercept the incidence of the excitation light and other stray light into the photodetector. If the excitation light is not effectively cut off or intercepted by means of the filter, the excitation light not cut off with the filter causes stray light ascribed to the refraction and reflection in the light path for measuring fluorescence, thereby causing noises in the fluorescence detection.

To reduce the noises in the fluorescent detection, it is desirable to excite a fluorescent dye with excitation light that is as weak as possible. For the detection of trace molecules, when the intensity of excitation light is increased for irradiation of a fluorescent dye so as to make a high fluorescence intensity and high sensitivity, noises simultaneously increases, resulting in the difficulty in improving the SN ratio. If a fluorescent dye is irradiated under an increased intensity of excitation light, some type of fluorescent dye that is not satisfactory in light resistance may undergo photodegradation.

In general, the detection sensitivity of a sample molecule labeled with a fluorescent dye, e.g. a biomolecule, depends on the difference between the wavelength (excitation wavelength) of excitation light exciting the fluorescent dye and the wavelength (fluorescence wavelength) of the fluorescence emitted from the fluorescent dye (i.e. the Stokes shift). If the Stokes shift is greater or the difference between the excitation wavelength and the fluorescence wavelength is greater and if a fluorescence to be detected is in a wavelength region that is more distant from that of the excitation light, the rate of elimination of stray light with a filter becomes higher, resulting in more reduction of noises. Where the Stokes shift is small, the detection of a fluorescence from a fluorescent dye is significantly impeded owing to the background noises ascribed to scattered excitation light, or background noises which are derived from the fluorescence of a co-existing substance in a sample containing a sample molecule. Thus, high sensitive measurement becomes difficult.

It is therefore preferable to provide a labeled compound and a detection method using the compound, which overcome the problems involved in the related art techniques.

It is also preferable to provide a labeled compound of the type which is so designed that an aromatic tertiary amine compound is enabled to be bound with a sample molecule and the sample molecule can be detected at high sensitivity and at a high SN ratio, and also to a detection method using such a labeled compound as mentioned above.

According to one embodiment, there is provided a labeled compound designed to enable an aromatic tertiary amine compound represented by the following general formula (1) to be bound with a sample molecule:

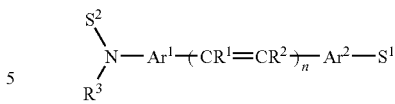

wherein n is 0 or 1, one of $S^1$ and $S^2$ represents a molecular chain-bound group wherein a molecular chain capable of binding with a sample molecule is bound to a divalent spacer having an alkyl chain that may have a divalent group selected from the following Gp1 at a main chain portion thereof, or a reactive group selected from the following Gp3, the other of $S^1$ and $S^2$ represents a group selected from the following Gp2, $R^1$ and $R^2$ may be the same or different and represent a group selected from a hydro group, an alkyl group and an aryl group that may contain a hetero atom, $R^3$ represents a group selected from a hydro group, an alkyl group that may have a substituent selected from the following Gp2, an aryl group that may have a substituent group, and a vinyl group that may have a substituent group, and $Ar^1$ and $Ar^2$ individually represent a divalent group and may be the same or different and represent an arylene group or a vinylene group wherein $Ar^2$ has at least one substituent group selected from an alkyl group, an aryl group, a cyano group, a trifluoromethyl group and a halo group and when n is 1, $Ar^1$ and $R^1$ or/and $Ar^2$ and $R^2$ may join together to form a ring, provided that Gp1 is a divalent group and represents an arylene group that may contain a hetero atom, a vinylene group, a carbonyl group, an oxy group, an oxycarbonyl group, a thio group, a sulfinyl group, a sulfonyl group, an imino group, a urylene group, an amide group or a silylene group, Gp2 is a monovalent group and represents a hydro group, an alkyl group, an aryl group, a vinyl group that may contain a substituent group, an amino group, a mercapto group, a hydroxy group, a carbamoyl group, a sulfino group, a sulfo group, a carboxy group or a halo group, and Gp3 is a monovalent group and represents an N-hydroxysuccinimide ester group, a hydroxysulfosuccinimide ester group, an imide ester group, an isothiocyanate group, an isocyanate group, a maleimide group, a carboxyl group, an aldehyde group, a glyoxal group, an imido ester group, an oxirane group (e.g. an epoxy group or a glycidyl ether group), a triazine group, a carbodiimide group, an aziridine group, a halogenated acyl group, a halogenated alkyl group, a halogenated sulfonyl group or a vinyl sulfone group.

According to another embodiment, there is also provided a detection method of a sample molecule using such a labeled compound as set forth above, the method including the steps of binding the above-defined labeled compound to a sample molecule, and detecting a fluorescence emitted from the labeled compound bound to the sample molecule by irradiation of light.

According to the embodiments, there can be provided a labeled compound which has a skeletal structure ensuring a high Stokes shift and a high fluorescence yield and is able to detect a sample molecule at high sensitivity and a high SN ratio. This labeled compound is higher in light resistance when compared with existing labeled compounds. When an excitation light intensity is increased for detection of trace molecules by photoexcitation of the labeled compound, there is little data variation as would be caused by photodegradation of the labeled compound.

According to the embodiments, there is also provided a detection method wherein a sample molecule can be detected at high sensitivity and a high SN ratio.

Additional features and advantages are described herein, and will be apparent from the following Detailed Description and the figures.

BRIEF DESCRIPTION OF THE FIGURES

FIG. 2 is a view showing examples of an aromatic amine fluorescent probe (first fluorescent probe) in an embodiment;

FIGS. 13A to 13D are views each illustrating an example of a solid phase support used in the synthesis of an oligonucleotide probe in an embodiment;

FIG. 16 is a chart of $^1$H-NMR spectra of the synthesized intermediate SP-1-OSu in the example;

DETAILED DESCRIPTION

Figure 1A:
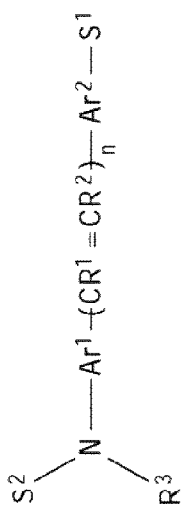
FIGS. 1A to 1C are views each illustrating an aromatic amine fluorescent probe in an embodiment.

In the labeled compound, it is preferred that $Ar^1$ is a phenyl group, $Ar^2$ is any of a phenylene group, a naphthylene group, a phenanthrylene group and an anthrylene group, and $R^1$ and $R^2$ are individually a hydro group, by which the afore-indicated general formula (1) can be re-formulated as represented by the following general formula (2):

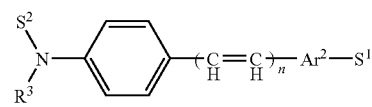

wherein $Ar^2$, $R^3$, $S^1$, $S^2$ and n, respectively, have the same meanings as defined before. In such re-formulation, the compound of the general formula (2) can be readily prepared according to the Wittig reaction (i.e. double bond-forming reaction) subsequent to the Vilsmeier reaction (aldehyde group introducing reaction) of a phenylamine. The compound of the general formula (2) becomes a compound whose resonant structure is highly stabilized by keeping the planarity between the phenylene group and the $(CH=CH)_n$ units. The molecular structure in an excited state greatly changes from the ground state owing to the degree of rotational freedom of the $(CH=CH)$ units, for which the Stokes shift becomes great.

In the formula (2), the compound is preferably so designed that $S^2$ is the afore-indicated molecular chain-bound group. By this, the compound can be readily prepared from commercially available reagents by several steps.

Further, it is preferred that the compound of the general formula (1) is so re-formulated as to provide a compound of the following general formula (3):

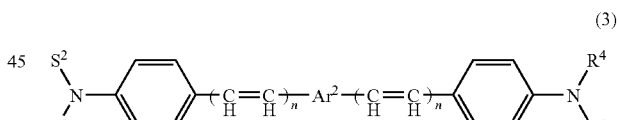

wherein $S^2$ is the afore-indicated molecular chain-bound group and $S^1$ is a 4-aminostyryl group. In doing so, there exist two aminostyryl moieties in the molecule and thus, the absorption coefficient of this compound becomes about double the case where there exists only one aminostyryl moiety, thereby ensuring a high utilization efficiency of excitation light.

In the formula (3), $R^4$ and $R^5$ may be the same or different and represent a group selected from a hydro group, an alkyl group that may has a substituent group and an aryl group that may have a substituent group.

Moreover, it is also preferred that the compound of the general formula (2) is so re-formulated as to provide a compound of the following general formula (4):

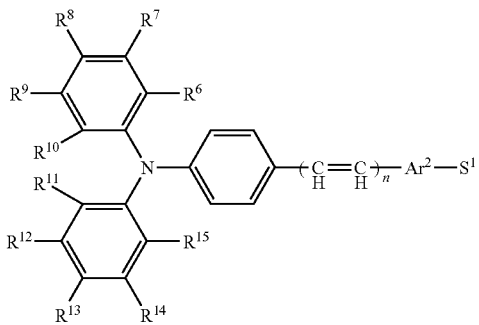

(4)

wherein $Ar^2$, $S^1$ and n, respectively, have the same meanings as defined before, and $S^2$ represents the molecular chain-bound group, which contains a phenyl group substituted with $R^6$, $R^7$, $R^8$, $R^9$ and $R^{10}$ provided that the afore-defined spacer is bound through the Gp1 to one of $R^6$, $R^7$, $R^8$, $R^9$ and $R^{10}$, the molecular chain is bound through the Gp1 to the spacer, and the others of $R^6$, $R^7$, $R^8$, $R^9$ and $R^{10}$ individually represent a hydro group, and $R^3$ is an aryl group containing a phenyl group substituted with $R^{11}$, $R^{12}$, $R^{13}$, $R^{14}$ and $R^{15}$ wherein $R^{11}$, $R^{12}$, $R^{13}$, $R^{14}$ and $R^{15}$ individually represent a group selected from the Gp2 provided that adjacent groups among the groups may join together to form a ring. In doing so, the bulkiness around the arylamino moiety can be increased, so that the quenching process ascribed to the interaction with other chemical substances co-existing in use can be reduced, thereby providing a compound having a high fluorescence yield.

Dfadf

Further, it is also preferred that the compound of the general formula (3) is re-formulated as to provide a compound represented by the following general formula (5):

wherein $Ar^2$ and n, respectively, have the same meanings as defined before, $S^2$ represents the molecular chain-bound group, which contains a phenyl group substituted with $R^6$, $R^7$, $R^8$, $R^9$ and $R^{10}$ provided that the spacer is bound through the Gp1 to one of $R^6$, $R^7$, $R^8$, $R^9$ and $R^{10}$, the molecular chain is bound through the Gp1 to the spacer, and the others of $R^6$, $R^7$, $R^8$, $R^9$ and $R^{10}$ represent a hydro group, $R^3$ represents an aryl group containing a phenyl group substituted with $R^{11}$, $R^{12}$, $R^{13}$, $R^{14}$ and $R^{15}$ provided that $R^{11}$, $R^{12}$, $R^{13}$, $R^{14}$ and $R^{15}$ are individually a group selected from the Gp2 and adjacent ones may join together to form a ring, $R^4$ represents an aryl group having a phenyl group substituted with $R^{16}$, $R^{17}$, $R^{18}$, $R^{19}$ and $R^{20}$, and $R^5$ is an aryl group having a phenyl group substituted with $R^{21}$, $R^{22}$, $R^{23}$, $R^{24}$ and $R^{25}$ wherein $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ individually represent a group selected from the Gp2 and adjacent groups among the groups may join together to form a ring. In doing so, two aminostyryl moieties exist in the molecule and thus, the absorption coefficient of this compound becomes about double the case where there exists only one aminostyryl moiety, thereby ensuring a high utilization efficiency of excitation light. Additionally, the bulkiness around the arylamino moieties can be increased, so that the quenching process ascribed to the interaction with other chemical substances co-existing in use can be reduced, thereby providing a compound having a high fluorescence yield.

Further, it is preferred that $S^1$ represents such a molecular chain-bound group as defined before. In doing so, the hydrophobic fluorophore (a component of a molecule which causes a molecule to be fluorescent) can be kept remote from a hydrophilic biomolecule, so that the quenching process and chemical reaction ascribed to the interaction between the dye and the biomolecule can be reduced.

Moreover, the compound of the general formula (3) can be so re-formulated or designed as to provide a compound represented by the following general formula (6):

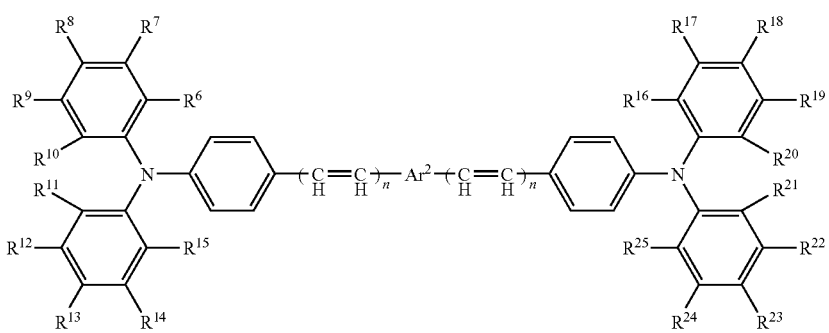

(5)

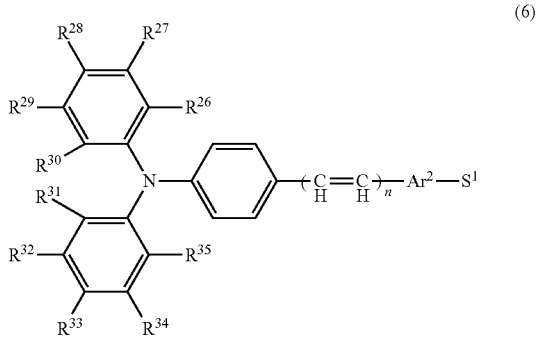

(6)

wherein $Ar^2$ and n, respectively, have the same meanings as defined before, $S^2$ is an aryl group having a phenyl group substituted with $R^{26}$, $R^{27}$, $R^{28}$, $R^{29}$ and $R^{30}$, $R^3$ is an aryl group having a phenyl group substituted with $R^{31}$, $R^{32}$, $R^{33}$, $R^{34}$ and $R^{35}$, and $R^{26}$, $R^{27}$, $R^{28}$, $R^{29}$, $R^{30}$, $R^{31}$, $R^{32}$, $R^{33}$, $R^{34}$ and $R^{35}$ individually represent a group selected from those of Gp2 provided that adjacent groups among the groups may join together to form a ring. In doing so, the bulkiness around the arylamino moiety can be increased and the quenching process ascribed to the interaction with other chemical substances co-existing in use and eventually, there can be provided a compound having a high fluorescence yield.

Preferably, the alkyl chain should have not smaller than 3 to not larger than 20 carbon atoms. This enables the distance between the hydrophobic fluorophore (fluorescent dye skeleton) and the hydrophilic biomolecule to be kept appropriately. Consequently, the quenching ascribed to the interaction between the dye and the biomolecule and the chemical reaction can be reduced. On the other hand, when the alkyl chain is too long, hydrophobicity undesirably increases for use as a labeled compound, with some possibility that interaction with a sample molecule is suppressed.

The sample molecule should preferably be one derived from a living body. By this, the living body-derived molecule can be detected at high sensitivity and a high SN ratio and can be detected by repeated light irradiation or by long-term light irradiation as would be difficult because of the thus far experienced unsatisfactory durability of dyes against light.

Moreover, the molecular chain should preferably be made up of an oligonucleotide. By this, the sample can be detected at high sensitivity and a high SN ratio as the result of the hybridization which is a double helix formation between the sample oligonucleotide and its complementary oligonucleotide strand bound to the labeled compound.

This oligonucleotide should preferably have a length of not smaller than 5 mer to not larger than 40 mer. This permits stable complementary binding between the sample oligonucleotide and its complementary oligonucleotide bound to the compound.

The oligonucleotide should preferably be so designed as to be used as a probe for detecting a complementary oligonucleotide strand of the living body-derived molecule having a complementary strand sequence thereof. This leads the complementary oligonucleotide strand to be detected at high sensitivity and a high SN ratio.

Preferably, the Gp3 is an N-hydroxysuccinimide ester group so as to permit an amino group contained in a sample molecule to be bound. In doing so, the sample molecule containing an amino group can be detected at high sensitivity and a high SN ratio.

Further, it is preferred that the Gp3 is preferably a maleimide group so as to permit a mercapto group contained in a sample molecule to be bound therewith. This allows the sample molecule containing a mercapto group to be detected at high sensitivity and a high SN ratio.

$R^3$ is preferably a phenyl group or a naphthyl group. In doing so, the bulkiness around the arylamino moiety can increase and thus, the quenching process derived from the interaction with other chemical substances co-existing in use can be reduced, with the result that there can be provided a compound having a high fluorescence yield.

$Ar^1$ is preferably a phenylene group or a naphthylene group. This permits ready synthesis from commercially available reagents by several steps. The bulkiness around the phenylamino moiety can increase, so that the quenching process ascribed to the interaction with other chemical substances co-existing in use can be reduced, thereby providing a compound having a high fluorescence yield.

$Ar^2$ is preferably one of a phenylene group, a naphthylene group, an anthrylene group and a phenanthlene group. In doing so, the resonance structure of a fluorophore (dye skeleton moiety) is stabilized and thus, a high fluorescence yield can be achieved.

In the afore-indicated general formula (1), $Ar^1$—$(CR^1=CR^2)_n$—$Ar^2$ (wherein n is 0 or 1) can be regarded as containing repeating units (C=C—) starting from the double bond of the $Ar^1$ moiety through $(CR^1=CR^2)_n$ to the double bond of $Ar^2$. In this sense, it is preferred that when the number of the repeating units is taken as m, such a structure of N—(C=C—)$_m$, (wherein m≧6) is established. By this, a maximum wavelength of a fluorescence created by the photoexcitation of the resulting labeled compound can be within a desired wavelength region and a great Stokes shift can be attained.

The labeled compound according to an example of the invention is a fluorescently-labeled compound which is able to emit a fluorescence by photoexcitation and is so designed that an aromatic tertiary amine compound (which may be hereinafter called merely aromatic amine in some cases) is bondable with a biomolecule. The labeled compound contains either a molecular chain-bound group wherein a molecular chain (e.g. an oligonucleotide) capable of binding with a sample molecule, e.g. a biomolecule, or a reactive group (e.g. an N-hydroxysuccinimide ester or a maleimide group) capable of covalent bonding with a reactive group (e.g. an amino group or a mercapto group) present in a biomolecule. This molecular chain-bound group or reactive group is bound directly or indirectly to amino N (nitrogen).

In the fluorescently-labeled compound according to the embodiment, the above-mentioned molecular chain is made up of an oligonucleotide, by which this oligonucleotide can be used as a probe for detecting a complementary oligonucleotide strand of a biomolecule having a complementary strand sequence, thereby enabling this complementary oligonucleotide strand to be detected at high sensitivity and a high SN ratio. In some cases, such a probe may be hereinafter referred to as an aromatic tertiary amine fluorescent probe (or abbreviated as an aromatic amine fluorescent probe or a fluorescent probe), or an oligonucleotide probe.

Where the fluorescently-labeled compound according to the embodiment is made up of an aromatic tertiary amine compound that has a reactive group capable of binding with a sample molecule, e.g. a biomolecule, this aromatic tertiary amine compound has reactive group A capable of binding with the biomolecule. Reactive group B which the biomolecule inherently has or which has been preliminarily imparted to the biomolecule and the reactive group A of the fluorescently-labeled compound form a covalent bond, so that the fluorescently-labeled compound and the biomolecule bind together. The detection of a fluorescence emitted by excitation of the fluorescently-labeled compound bound to the biomolecule leads to the detection of the sample biomolecule at high sensitivity and a high SN ratio.

The labeled compound according to the embodiment of the invention has any of a phenyl group or a naphthyl group bound to amino N, a phenylene group or a naphthylene group bound to amino N, and a phenylene group, a naphthylene group, an anthrylene group or a phenanthrene group bound directly or indirectly to the phenylene or naphthylene group bound to amino N. $Ar^1—(CR^1=CR^2)_n—Ar^2$ (wherein n is 0 or 1) in the foregoing general formula (1) contains repeating units (C=C—) and has N—$(C=C—)_m$ wherein $m \geq 6$ when the number of the repeating units is taken as m.

It will be noted that the molecular chain-bound group or the reactive group is bound to any of a phenyl group or a naphthyl group bonded to amino N and a phenylene group, a naphthylene group, an anthrylene group or a phenanthrene group directly or indirectly bound to the phenylene group or naphthylene group bound to amino N.

Because of the presence of the repeated units (C=C—), the peak wavelength of a fluorescence resulting from the photoexcitation of the labeled compound can be within a desired wavelength region, the Stokes shift can be made great and satisfactory light resistance is ensured. The fluorescence emitted by excitation through photoirradiation of the labeled compound bound to the biomolecule is detected, thus enabling the target biomolecule to be detected at high sensitivity and a high SN ratio.

With the fluorescent probe based on the labeled compound according to the embodiment or the detection method using the fluorescently-labeled compound covalently bonded to a sample molecule, the sample molecule (or target molecule) to be detected consists of a biomolecule such as a living body-derived molecule, a physiologically active molecule or the like, and such a biomolecule can be detected at high sensitivity and a high SN ratio.

The biomolecule includes those, for example, of enzymes, proteins, sugars, nucleic acids, oligonucleotides, fats, amino acids and the like. The proteins include, for example, antibodies and derivatives thereof, antigens and derivatives thereof, avidins including streptoavidin, serum albumins, hates, hormones and the like. The embodiments are applicable to the detection of chemical substances such as diagnostic medicines, curing medicines and the like, environmental substances causing diseases such as allergies and the like.

Embodiments are now described in detail with reference to the accompanying drawings.

Embodiment

Figure 1B:
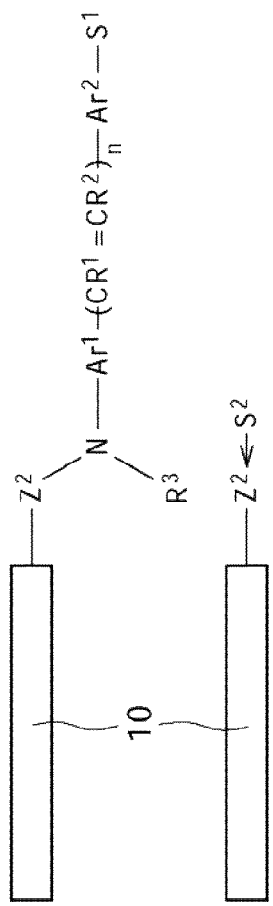
Figure 1C:
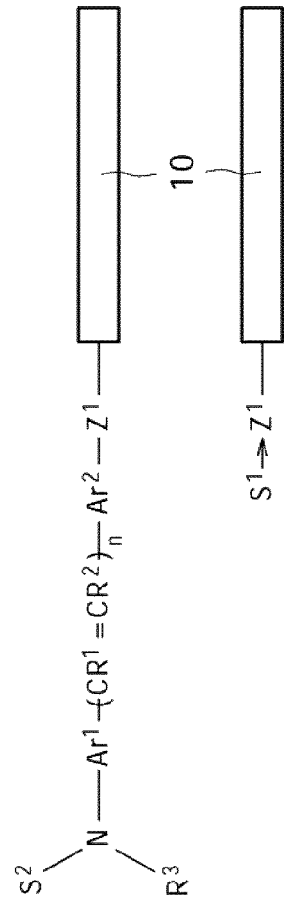

FIGS. 1A to 1C individually illustrate labeled compounds according to embodiments. FIG. 1A shows the chemical structure of a labeled compound wherein $S^1$ or $S^2$ is a molecular chain-bound group in which a molecular chain capable of binding with a biomolecule is bound or is a reactive group capable of covalently bonding with a reactive group of a biomolecule. FIG. 1B is the chemical structure of a labeled compound (probe) wherein $S^1$ is a molecular chain-bound group whose molecular chain 10 capable of binding with a biomolecule is bound to a spacer (linker) $Z^1$, and FIG. 1C is the chemical structure of a labeled compound (probe) wherein $S^2$ is a molecular chain-bound group whose molecular chain 10 capable of binding with a biomolecule is bound to a spacer (linker) $Z^2$.

In the labeled compound shown in FIG. 1A, n is 0 or 1, one of $S^1$ or $S^2$ is a molecular chain-bound group which has a molecular chain capable of binding with a biomolecule bound to a divalent spacer containing an alkyl group that may contain a divalent group selected from the following Gp1 at a main chain portion thereof, or which has a reactive group selected from the following Gp3, and the other of $S^1$ and $S^2$ is a group selected from the following Gp2.

In the formulas, $R^1$ and $R^2$ may be the same or different and represent a group selected from a hydro group, an alkyl group and aryl group that may contain a hetero atom, $R^3$ is a group selected from a hydro group, an alkyl group that may have a substituent group selected from the following Gp2, an aryl group that may has a substituent group, and a vinyl group that may have a substituent group.

$Ar^1$ and $Ar^2$ represent a divalent group and may be the same or different and particularly represent an arylene group or a vinylene group wherein $Ar^2$ has at least one substituent group selected from an alkyl group, an aryl group, a cyano group (—CN), a tri fluoromethyl group (—$CF_3$) and a halo group, and when n is at 1, $Ar^1$ and $R^1$ or/and $Ar^2$ and $R^2$ may join together to form a ring.

For instance, $R^3$ is a phenyl group (—$C_6H_5$) or a naphthyl group (—$C_{10}H_7$), $Ar^1$ is a phenylene group (—$C_6H_4$—) or a naphthylene group (—$C_{10}H_6$—), $Ar^2$ is any of a phenylene group, a naphthylene group, an anthrylene group (—$C_{14}H_8$—) and a phenanthrene group (—$C_{14}H_{10}$—), and $R^1$ and $R^2$ are individually a hydro group (—H).

Gp1 is a divalent group and includes an arylene group that may contain a hetero atom (i.e. a group formed by withdrawing one hydrogen atom from an aryl group or a group formed by withdrawing one hydrogen atom from a monocyclic or polycyclic aromatic ring-bearing aromatic compound and heteroaromatic compound), a vinylene group (—CH=CH—), a carbonyl group —(CO—), an oxy group (—O—), an oxycarbonyl group (—O—CO—), a thio group (—S—), a sulfinyl group (—SO—), a sulfonyl group (—$SO_2$—), an imino group (—NH—), a urylene group (—NHCONH—), an amide group ($H_2NC(O=NH)$—) or a silylene group (—$SiH_2$—). Preferably, Gp1 is an arylene group, a vinylene group or a carbonyl group.

Gp2 is a monovalent group and includes a hydro group (—H), an alkyl group (—$C_nH_{2n+1}$), an aryl group, a vinyl group (—CH=$CH_2$) that may contain a substituent group, an amino group (—$NH_2$), a mercapto group (—SH), a hydroxy group (—OH), a carbamoyl group ($H_2NCO$—), a sulfino group (—$SO_2H$), a sulfo group (—$SO_3H$), a carboxy group (—COOH) or a halo group (i.e. a halogen group such as —F, —Cl, —Br or —I). Preferably, Gp2 is a hydro group, an alkyl group or a vinyl group.

Gp3 is a monovalent group and includes an N-hydroxysuccinimide ester group, a hydroxysulfosuccinimide ester group, an imide ester group, an isothiocyanate group, an isocyanate group, a maleimide group, a carboxyl group, an aldehyde group, a glyoxal group, an imidoester group, an oxirane group (an epoxy group, a glycidyl ether group), a triazine group, a carbodiimide group, an aziridine group, a halogenated acyl group, a halogenated alkyl group, a halogenated sulfonyl group or a vinylsulfone group. Preferably, Gp3 is an N-hydroxysuccinimide ester group or a maleimide group.

The labeled compound shown in FIG. 1B is a fluorescent probe wherein in the labeled compound of FIG. 1A, —$S^1$ is replaced by —$Z^1$— (a molecular chain 10 capable of binding with a biomolecule). $Z^1$ is a divalent spacer (linker) containing an alkyl chain, which may contain a divalent group selected from the Gp1, at a main chain thereof.

The labeled compound shown in FIG. 1C is a fluorescent probe wherein —$S^2$ in the labeled compound of FIG. 1A is replaced by —$Z^2$— (a molecular chain 10 capable of binding with a biomolecule). $Z^2$ is a divalent spacer (linker) containing an alkyl chain, which may contain a divalent group selected from the Gp1, at a main chain thereof.

As will be seen from FIGS. 1B and 1C, the fluorescent probes are, respectively, made of an aromatic tertiary amine compound having the molecular chain capable of binding with a biomolecule bonded thereto and the molecular chain 10 capable of binding with the biomolecule is bound to the linker group $Z^1$ or $Z^2$.

In the labeled compounds having such structures as shown in FIGS. 1B and 1C, the molecular chain 10, which is bondable with a biomolecule, is made, for example, of a nucleotide having a length of not smaller than 5 mer and larger than 40 mer.

In the labeled compound shown in FIG. 1A, where one of $S^1$ and $S^2$ contains a reactive group A, a biomolecule should inherently have a reactive group B capable of binding with the reactive group A or should be introduced with the reactive group B thereinto. The labeled compound has the reactive group A that is necessary for binding with a biomolecule serving as a sample, e.g. a protein or a nucleic acid, for which if the biomolecule is so designed that it inherently has or is preliminarily imparted with the reactive group B capable of reaction with the reactive group A, the biomolecule and the labeled compound form a covalent bond therebetween according to a known technique and bind together.

Possible combinations of the reactive group A and the reactive group B capable of forming the covalent bond include, for example, amino group/carboxyl group, amino group/halogenated acyl group, amino group/N-hydroxysuccinimide ester group, amino group/aldehyde group, mercapto group/maleimide group, mercapto group/vinyl sulfonate group, hydroxyl group/carboxyl group and the like. Preferable combinations of the reactive group B and reactive group A include amino group/N-hydroxysuccinimide ester group and mercapto group/maleimide group.

The labeled compounds having such structures as shown in FIGS. 1A to 1C are such that $Ar^1$—$(CR^1=CR^2)_n$—$Ar^2$ wherein n is 0 or 1 has repeating units of (C=C—) and when the number of the repeating units is taken as m, the compound has N—$(C=C—)_m$ wherein m≧6.

The case where the labeled compound of FIG. 1A is applied as a fluorescent probe as shown in FIG. 1B or 1C is now described.

Figure 3:
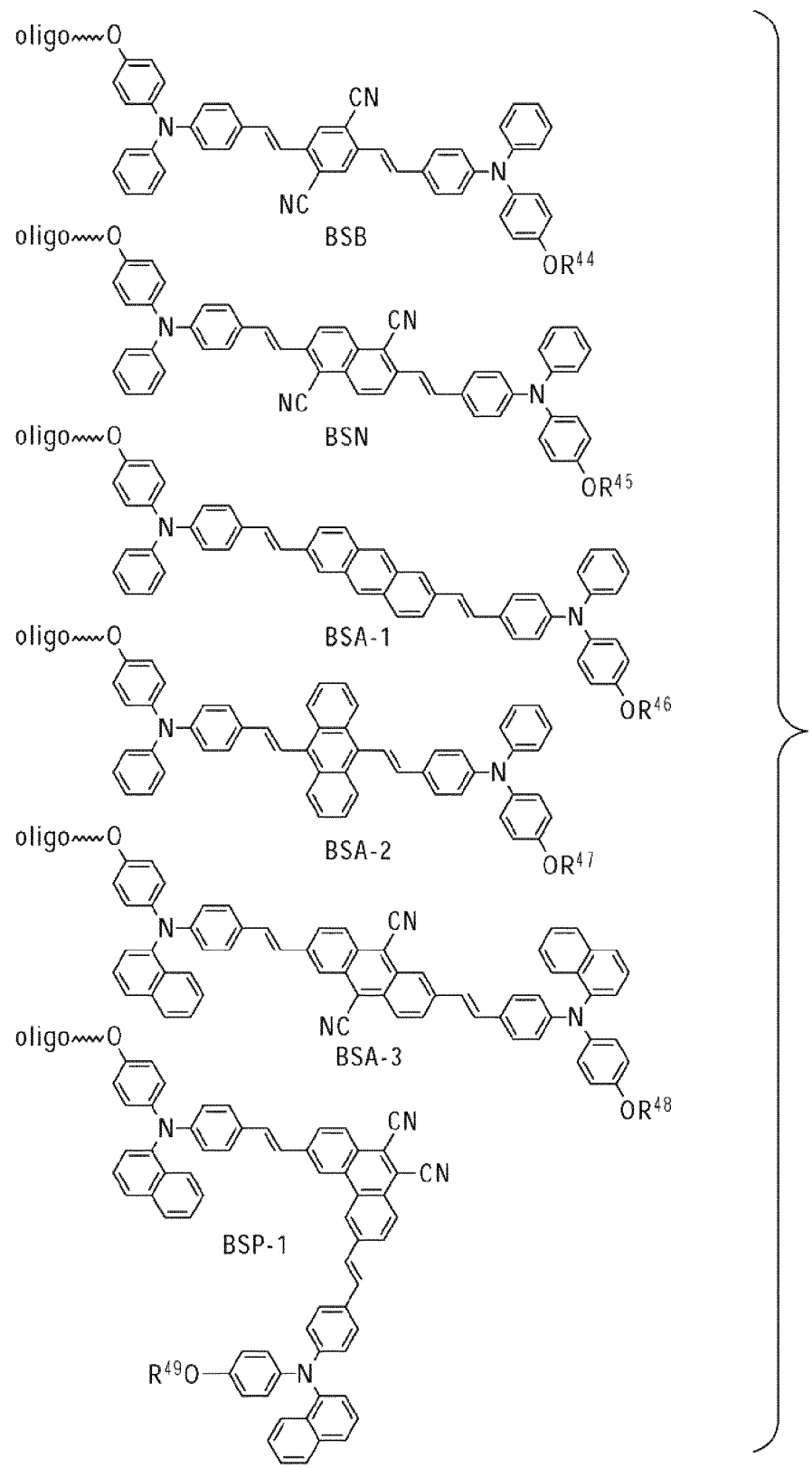
FIG. 3 is a view showing examples of an aromatic amine fluorescent probe (first fluorescent probe) in an embodiment.

FIGS. 2 and 3 show examples of an aromatic amine fluorescent probe (first fluorescent probe) in an embodiment.

The first fluorescent probes shown at the left side of FIG. 2 correspond to the labeled compound of FIG. 1B. With this first fluorescent probe, n is 1, and $S^2$ contains a phenyl group to which an oxy group is bound wherein an oligonucleotide (oligo) is indirectly bound to the oxy group, $R^3$ is a phenyl group or a naphthyl group, $Ar^1$ is a phenylene group, $Ar^2$ is a structure of any of a phenylene group, a naphthylene group, an anthrylene group and a phenanthrylene group which is unsubstituted or has a substituent group $S^1$ wherein $S^1$ is a methyl group or/and a cyano group. $R^1$ and $R^2$ are individually a hydro group.

The first fluorescent probes shown at the right side of FIG. 2 correspond to the labeled compound shown in FIG. 1C. With this first fluorescent probe, n is 1, and $S^2$ contains a phenyl group to which an oxy group is bound, $R^3$ is a phenyl group or a naphthyl group, and $Ar^1$ is a phenylene group. $Ar^2$ is a structure of any of a phenylene group, a naphthylene group, an anthrylene group and a phenanthrylene group, which is unsubstituted or has a cyano group as a substituent group and has a divalent group —$CH_2O$— (oxymethylene group) or an oxy group to which an oligonucleotide (depicted as oligo) is indirectly bound. $R^1$ and $R^2$ are individually a hydro group.

The first fluorescent probes shown in FIG. 3 correspond to the labeled compound of FIG. 1B. With this first probe, n is 1, $S^2$ contains a phenyl group to which an oxy group is bound wherein an oligonucleotide (oligo) is bound indirectly to the oxy group. $R^3$ is a phenyl group or a naphthyl group, $Ar^1$ is a phenylene group. $Ar^2$ is a structure of any of a phenylene group, a naphthylene group, an anthrylene group and a phenanthrylene group, which is unsubstituted or has a cyano substituent group. In addition, $Ar^2$ is bound with —CH=CH—, to which a phenyl group bound to amino N, or a phenyl group or an aromatic tertiary amine compound having a phenyl group and a naphthyl group is bound. $R^1$ and $R^2$ are individually a hydro group.

Figure 4:
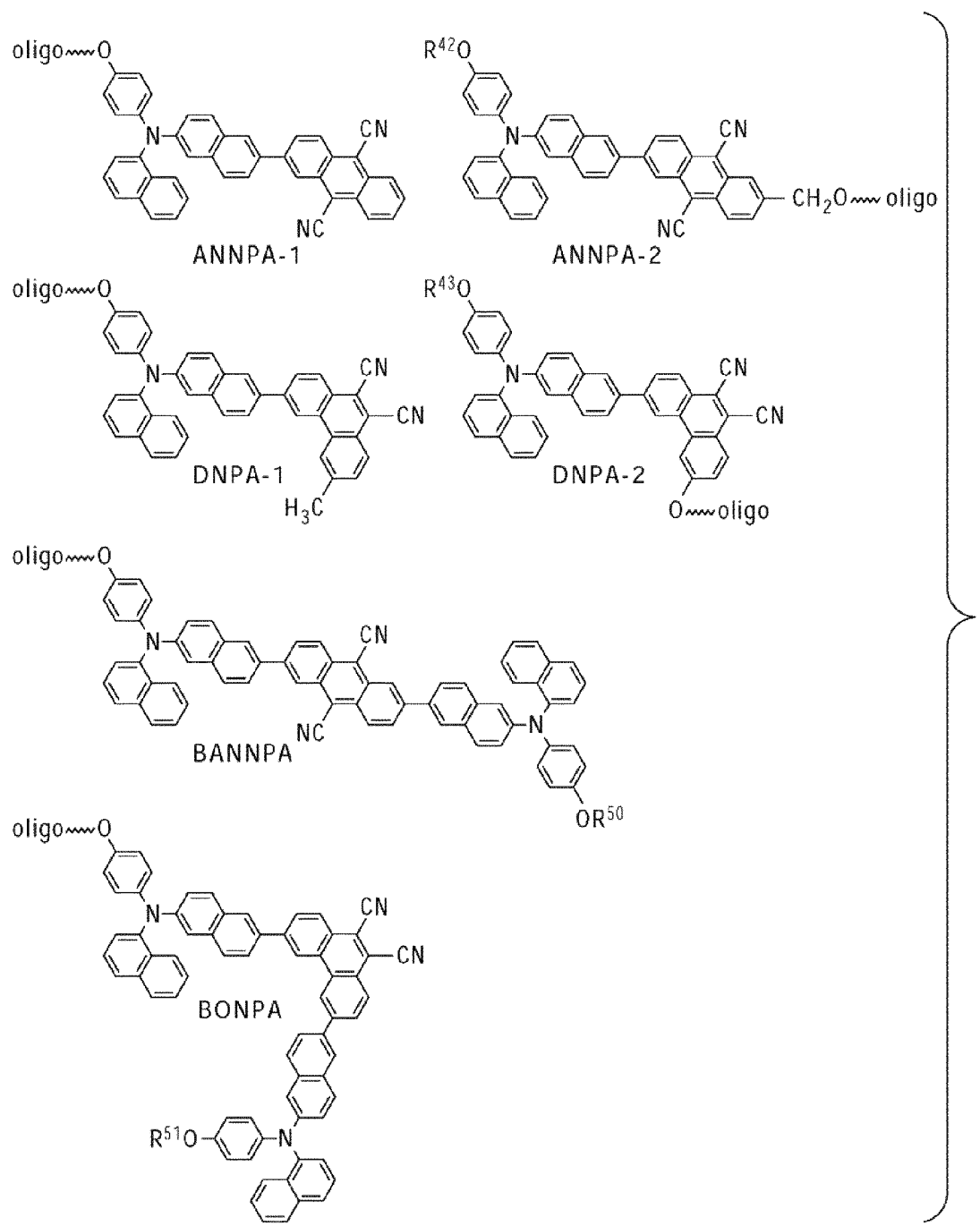
FIG. 4 is a view showing examples of an aromatic amine fluorescent probe (second fluorescent probe) in an embodiment.

FIG. 4 shows examples of an aromatic amine fluorescent probe (second fluorescent probe) in an embodiment.

The two second fluorescent probes indicated at the upper portion of the left side of FIG. 4 correspond to the label compound of FIG. 1B. This second fluorescent probe is such that n is 0, $S^2$ contains a phenyl group to which an oxy group is bound and an oligonucleotide (oligo) is bound indirectly to the oxy group. Moreover, $R^3$ is a naphtyl group, $Ar^1$ is a naphthylene group, $Ar^2$ is an anthrylene group or a phenanthrylene group having a substituent group $S^1$ wherein $S^1$ is a methyl group or/and a cyano group.

The two second fluorescent probes indicated at the upper portion of the right side of FIG. 4 correspond to the labeled compound shown in FIG. 1C. This second fluorescent probe is such that n is 0, $S^2$ contains a phenyl group to which an oxy group is bound. $R^3$ is a naphtyl group, $Ar^1$ is a naphthylene group, $Ar^2$ is an anthrylene group or a phenanthrylene group which has a cyano group as a substituent group and also has a divalent group —$CH_2O$— (oxymethylene group whose oxy group is indirectly bound to an oligonucleotide (oligo) or an oxy group.

The two second fluorescent probes indicated at the lower portion of the left side of FIG. 4 correspond to the labeled compound shown in FIG. 1B. This second fluorescent probe is such that n is 0, $S^2$ contains a phenyl group to which an oxy group is bound wherein an oligonucleotide (oligo) is bound indirectly to the oxy group. $R^3$ is a naphtyl group, $Ar^1$ is a naphthylene group, $Ar^2$ is an anthrylene group or a phenanthrylene group which has a cyano group as a substituent group and is bound with a naphthyl group of an aromatic tertiary amine compound having a phenyl group and a naphthyl group bound to amino N.

In FIGS. 2, 3 and 4, the names of the aromatic amine compounds are expressed as abbreviations consisting of alphanumeric mixes indicated in the figures and the abbreviation is taken in the name of the fluorescent probe thereby showing the structure of an aromatic amine compound used in the fluorescent probe (which is true of figures other than FIGS. 2, 3 and 4 and appearing hereinafter and related descriptions thereof).

In FIGS. 2, 3 and 4, $R^{36}$ to $R^{51}$ individually represent a substituent group selected from a hydro group, an alkyl group, an aryl group, a vinyl group that may contain a substituent group, an amino group, a mercapto group (thiole group), a hydroxy group, a carbamoyl group, a sulfino group, a sulfo group, a carboxy group and a halo group.

In the examples of the fluorescent probes of FIGS. 2 and 3, $Ar^1$ in the general formula (1) is a phenylene group, $R^3$ is a phenyl group or a naphthyl group, $R^1$ and $R^2$ are individually a hydro group, and $Ar^2$ is a phenylene group, a naphthylene group, a phenanthrylene group or an anthrylene group. In the examples of the fluorescent probes shown in FIG. 4, $Ar^3$ in the general formula (2) is a naphthylene group, $R^4$ is a naphthyl group, and $Ar^4$ is a phenanthrylene group or an anthrylene group.

In FIGS. 2, 3 and 4, the term "oligo" means an oligonucleotide that is a molecular chain bondable with a biomolecule and this oligo is bound to $S_1$ or $S_2$ of the aromatic amine compound at the 5' or 3' terminal thereof.

Next, the above-mentioned abbreviations in the figures are illustrated. In FIGS. 2, 3 and 4, in case where the first letter of the abbreviations starts from B, such an abbreviation indicates "diamine," and the others indicate "monoamine."

In the abbreviations used in FIGS. 2, 3, S indicates such a structure that in the triphenylamine $((C_6H_5)_3N)$ moiety, one hydro group of the first phenyl group ($—C_6H_5$) is substituted with an oxy group ($—O—$) and one hydro group of the second phenyl group is substituted with a vinylene group ($—CH=CH—$). The third phenyl group of the triphenylamine moiety may be substituted with a naphthyl group ($—C_{10}H_7$), which may be regarded as a triphenylamine derivative and is thus called triphenylamine moiety, like the former cases. The fluorescent probes are provided with structures having B, N, A and P explained hereinbelow and bound to the above-mentioned vinylene group.

B indicates a styrylene group ($—C_6H_4CH=CH—$), N indicates a naphthyl group ($—C_{10}H_7$) having a substituent group, A indicates an anthryl group ($—C_{14}H_9$) that may have a substituent group, and P indicates a phenanthryl group ($—C_{14}H_9$) having a substituent group.

The aromatic amine fluorescent probes shown in FIG. 4 are made of tertiary amine compounds, which have such structures that in the triphenylamine moiety $((C_6H_5)_3N)$, one hydro group ($—H$) of the first phenyl group is substituted with an oxy group ($—O—$), the second phenyl group is substituted with a naphtyl group ($—C_{10}H_7$), and the third phenyl group is substituted with a naphthylene group ($—C_{10}H_6—$) and to which a molecular chain (oligonucleotide, abbreviated as oligo in the figure) capable of binding with a biomolecule is added or (bound). In the figure, the fluorescent probe having an anthrylene group bound to the naphthylene group of the tertiary amine compound is indicated as ANNPA and the fluorescent probe having a phenanthrylene group bound to the naphthylene group of the tertiary amine compound is indicated as DNPA.

As shown in FIGS. 2, 3 and 4, an alkyl group is bound to the oxy group or oxymethylene group ($—CH_2O—$) with which the hydro group of the benzene ring is substituted, or the oxymethylene group ($—CH_2O—$) with which the hydro group of the naphthalene ring is substituted, or the oxymethylene group ($—CH_2O—$) with which the hydro group of the anthracene ring is substituted, or the oxy group with which the hydro group of the phenanthrene ring is substituted, to which the oligo is bound.

The fluorescent probes shown in FIGS. 2, 3 and 4 contain repeating units ($C=C—$) and the number m of the repeating units differs depending on the structure of the fluorescent probe.

In the aromatic monoamine fluorescent probe shown in FIG. 2, fluorescent probes having the abbreviation SB are provided with a structure wherein the benzene ring is bound to a vinylene group of the triphenylamine moiety to which the vinylene group is bound and the number of repeating units ($C=C—$) is 6.

The fluorescent probes SN-1 and SN-2 are individually provided with a structure wherein a naphthalene ring is bound to a vinylene group of the triphenylamine moiety to which the vinylene group is bound and the number of repeating units ($C=C—$) is 7.

The fluorescent probes SA-1 to SA-6 are individually provided with a structure wherein an anthracene ring is bound to a vinylene group of the triphenylamine moiety to which the vinylene group is bound and the number of repeating units ($C=C—$) is 9 for SA-1, SA-2, SA-5 and SA-6 and is 10 for SA-3 and SA-4.

The fluorescent probes SP-1 and SP-2 are individually provided with a structure wherein a phenanthrene ring is bound to a vinylene group of the triphenylamine moiety to which the vinylene group is bound and the number of repeating unit ($C=C—$) is 9.

The aromatic amine fluorescent probes BSB and BSN shown in FIG. 3 are individually provided with a structure wherein a benzene ring and a naphthalene ring are individually bound to the vinylene group of the two triphenylamine moiety to which the vinylene ring is bound, and the numbers of repeating units ($C=C—$) are 8 and 10 for BSB and BSN, respectively.

The fluorescent probes BSA-1 to BSA-3 are individually provided with a structure wherein an anthracene ring is bound to vinylene group of the two triphenylamine moieties to which the vinylene group is bound, and the number of repeating units ($C=C—$) is 11 for both.

The fluorescent probe BSP-1 is provided with a structure wherein a phenanthrene ring is bound to a vinylene group of each of the two triphenylamine moieties to which the vinylene group is bound and the number of repeating units ($C=C—$) is 12.

The aromatic monoamine fluorescent probes, abbreviated as ANNPA-1 and ANNPA-2, shown in FIG. 4 are provided with a triphenyleneamine structure wherein two benzene rings are, respectively, substituted with a naphthyl ring and a structure wherein an anthracene ring is bound to the triphenylamine moieties, and the number of repeating units ($CH=CH—$) is 9.

The fluorescent probes, abbreviated as DNPA-1 and DNPA-2, are provided with a triphenylamine moiety wherein two benzene rings are, respectively, substituted with a naphthyl ring and a structure wherein a phenanthrene ring is bound to the former moiety, and the number of repeated units ($C=C—$) is 9.

The fluorescent probe BANNPA is provided with a structure wherein an anthracene ring is bound between two triphenylamine moieties whose two benzene rings are substituted with a naphthyl ring, and the number of repeating units ($C=C—$) is 11.

The fluorescent probe BDNPA is provided with a structure wherein an phenanthrene ring is bound between two triphenylamine moieties whose two benzene rings are substituted with a naphthyl ring, and the number of repeating units ($C=C—$) is 12.

Figure 5:
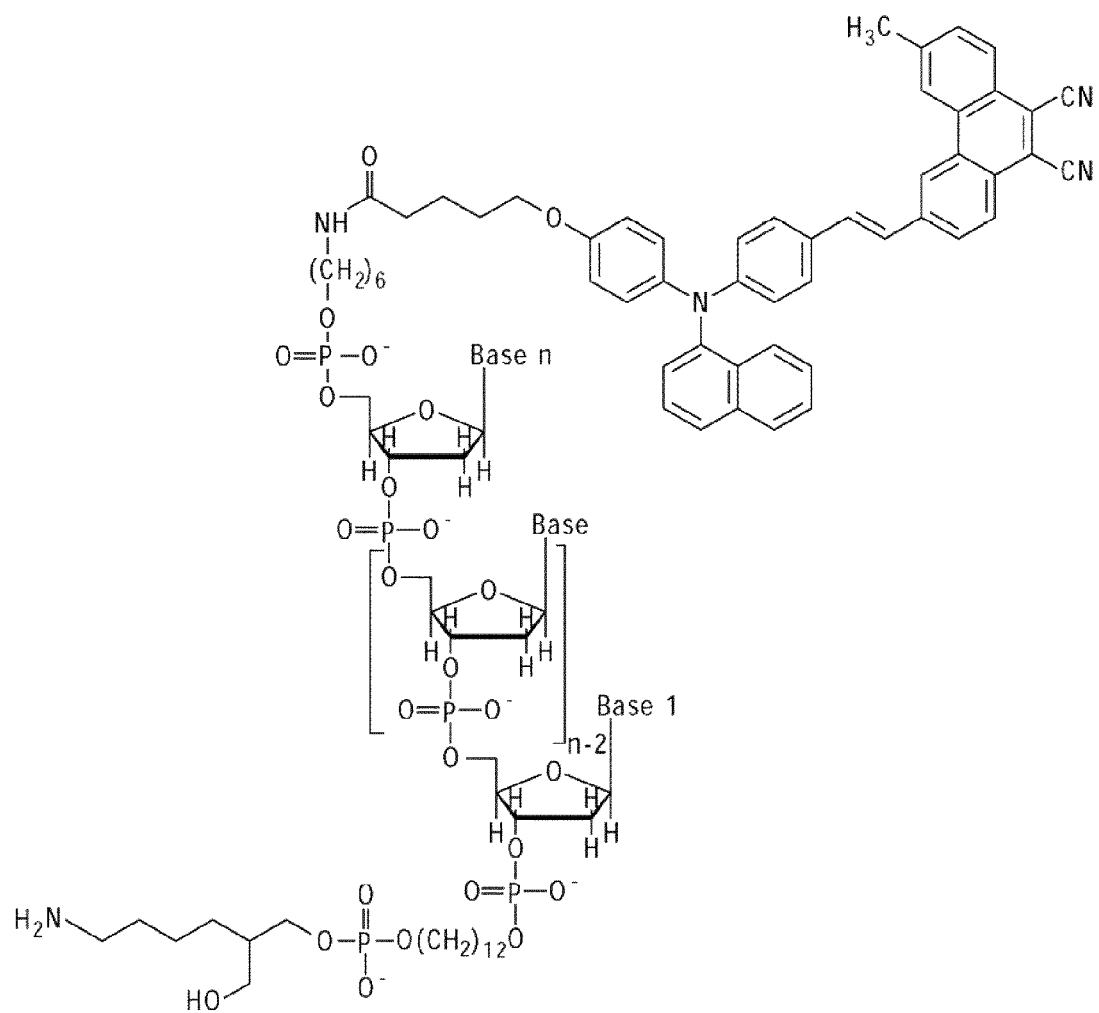
FIG. 5 is a view showing an example of an aromatic amine fluorescent probe and illustrating a 3'-amino-5'-SP-1-oligonucleotide probe in an embodiment.

FIG. 5 is a view showing an example of an aromatic amine fluorescent probe embodying the invention and more specifically, is a view illustrating a 3'-amino-5'-SP-1-oligonucleotide probe.

The fluorescent probe of FIG. 5 has such a structure as shown in FIG. 1A and corresponds to SP-1 shown in FIG. 2 wherein the molecular chain 10 capable of binding with a biomolecule is bound to an aromatic tertiary amine compound. This probe corresponds to A17 appearing hereinafter in FIG. 10.

This molecular chain 10 contains an oligonucleotide made of an n number of nucleotides and this oligonucleotide consists of bonded nucleotides (which may be analogue nucleotides) having a base selected from A, T, G and C. It will be noted that in FIG. 5, (n–2) indicates an Nth (wherein N=2, 3, . . . , (n–1)) nucleotide (base N(=2, 3, . . . , (n–1)) (which is true of FIGS. 6 to 12 appearing hereinafter).

The oligonucleotide has —$(PO^{4-})(CH_2)_6NH$— at the 5' terminal and —$(PO^{4-})$ $(CH_2)_{12}(PO^{4-})(CH_2)CH(CH_2OH)(CH_2)_4NH_2$ at the 3' terminal. The NH— at the 5' terminal side of the oligonucleotide of the molecular chain 10 is bound to the aromatic tertiary amine compound SP-1 and the 3' terminal side is terminated with $NH_2$.

In FIG. 5, $S^1$, $Ar^2$, $Ar^1$, $R^3$ and $S^2$ in the formula of FIG. 1A are, respectively, such that ($Ar^2$—S1) is —$C_{14}H_6(CN)_2CH_3$, $Ar^1$ is —$C_6H_4$—, $R^3$ is —$C_{10}H_7$, $S_2$ is —$C_6H_4O(CH_2)_4CO$—.

The synthesis of the 3'-amino-5'-Sp-1-oligonucleotide probe shown in FIG. 5 is described hereinafter with reference to FIGS. 8, 9 and 10.

Figure 6:
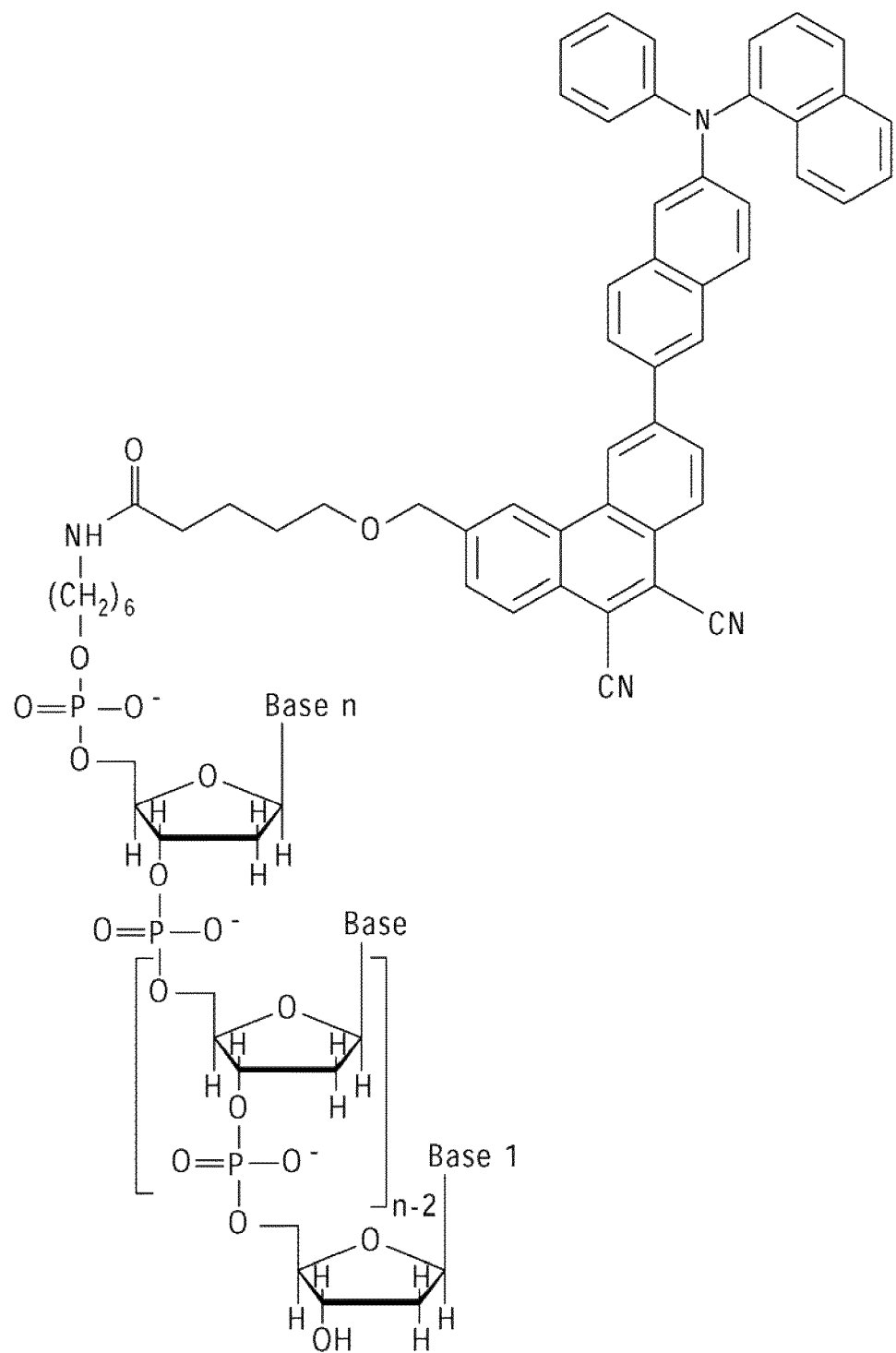
FIG. 6 is a view showing an example of an aromatic amine fluorescent probe and particularly illustrating a 5'-DNPA-oligonucleotide probe in an embodiment.

FIG. 6 shows an aromatic amine fluorescent probe according to an embodiment of the invention, particularly, a 5'-DNPA-oligonucleotide probe.

The fluorescent probe shown in FIG. 6 has such a structure as shown in FIG. 1D wherein the molecular chain 10 capable of binding with a biomolecule is bound to an aromatic amine compound (DNPA-2, shown in FIG. 4, provided that —$OR^{43}$ is replaced by —H).

This molecular chain 10 contains an oligonucleotide consisting of an n number of nucleotides as with the case of FIG. 5. The oligonucleotide has $(PO^{4-})(CH_2)_6NH$— at the 5' terminal and —OH at the 3' terminal. The NH— at the 5' terminal side of the oligonucleotide of the molecular chain 10 is bound to the DNPA-2 of the aromatic amine compound and the 3' terminal side is terminated with OH.

In FIG. 6, $S^4$, $R^4$, $Ar^3$, $Ar^4$ and $S^3$ shown in FIG. 1D are such that $S^4$ is —$C_6H_5$, $R^4$ is —$C_{10}H_7$, $Ar^3$ is —$C_{10}H_6$—, $Ar^4$ is —$C_{14}H_6(CN)_2$—, and $S^3$ is —$CO(CH_2)_4CO$—.

Figure 7:
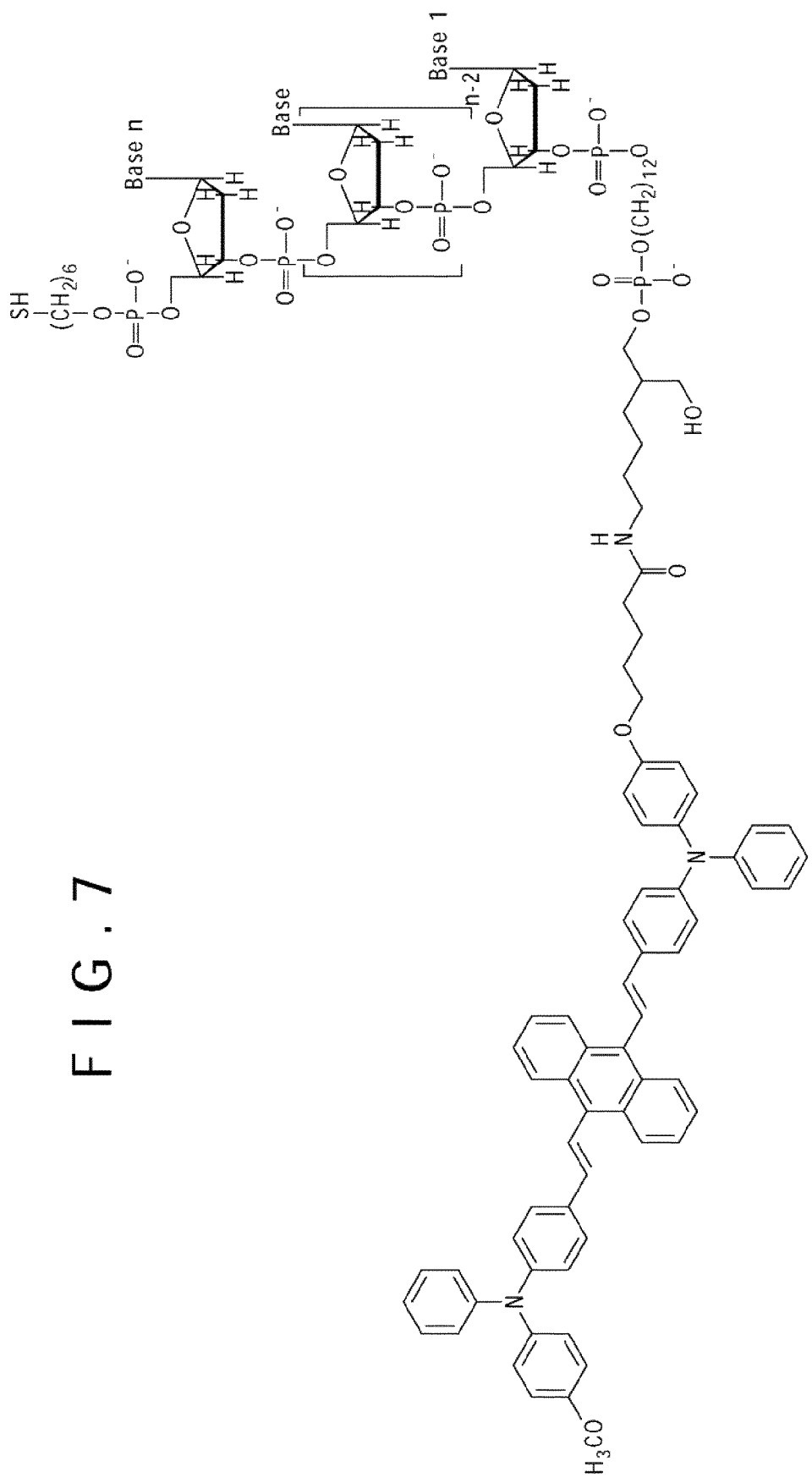
FIG. 7 is a view showing an example of an aromatic amine fluorescent probe and particularly illustrating a 3'-BSA1-5'-thio-oligonucleotide probe in an embodiment.

FIG. 7 shows an example of an aromatic amine fluorescent probe embodying the invention, particularly, a 3'-BSA-2-5'-thio-oligonucleotide probe.

The fluorescent probe shown in FIG. 7 has the structure of FIG. 1A wherein the molecular chain 10 capable binding with a biomolecule is bound to an aromatic amine compound (BSA-2 shown in FIG. 3 provided that $R^{47}$=$CH_3$). The aromatic amine compound BSA-2 has a structure wherein —$(C_6H_4)N(C_6H_5)(C_6H_4)$— is bound to the anthrylene group (—$C_{14}H_8$—) at opposite ends thereof.

This molecular chain 10 contains an oligonucleotide consisting of an n number of oligonucleotides as with the case of FIG. 5. The oligonucleotide has $(PO^{4-})(CH_2)_{12}(PO^{4-})(CH_2)CH(CH_2OH)(CH_2)_4NH$— at the 3' terminal and —$(PO^{4-})(CH_2)_6SH$— at the 5' terminal. The NH— at the 3' terminal side of the oligonucleotide of the molecular chain 10 is bound to the BSA-2 of the aromatic amine compound and the 5' terminal side is terminated with SH.

In FIG. 7, $S^1$, $Ar^2$, $Ar^1$, $R^3$ and $S^2$ shown in FIG. 1A are such that $S^1$ is —$CHCHC_6H_4N(C_6H_5)(C_6H_4OCH_3)$, $Ar^2$ is —$C_{14}H_8$—, $Ar^1$ is —$C_6H_4$—, $R^3$ is —$C_6H_5$— and $S^2$ is —$C_6H_4O(CH_2)_4CONH$—.

Figure 8:
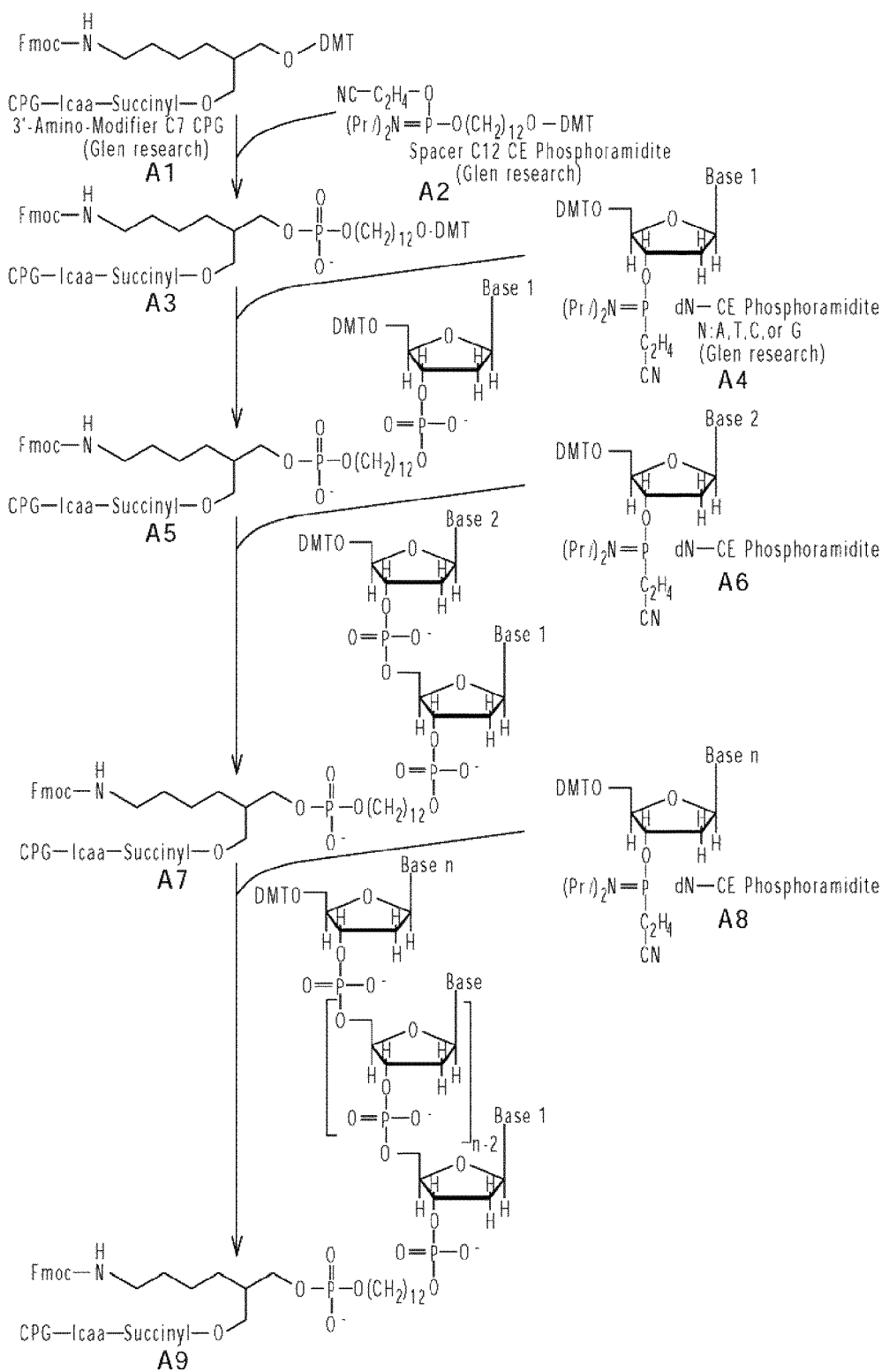
FIG. 8 is a view showing an example of a synthetic scheme of an aromatic amine fluorescent probe and particularly illustrating a synthetic scheme of 3'-amino-5'-SP-1-oligonucleotide probe in an embodiment.
Figure 9:
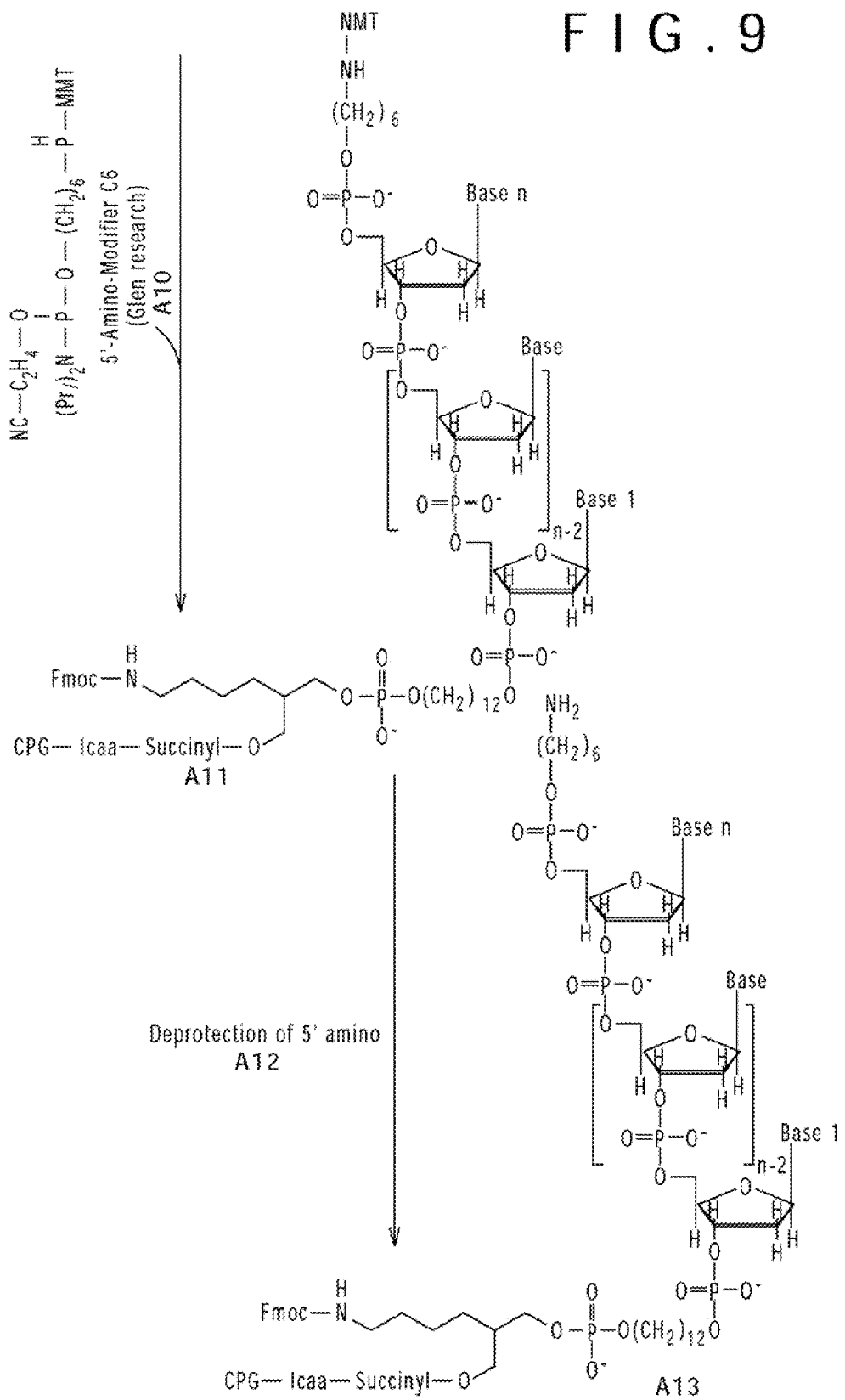
FIG. 9 is a view subsequent to the synthetic scheme of FIG. 8.
Figure 10:
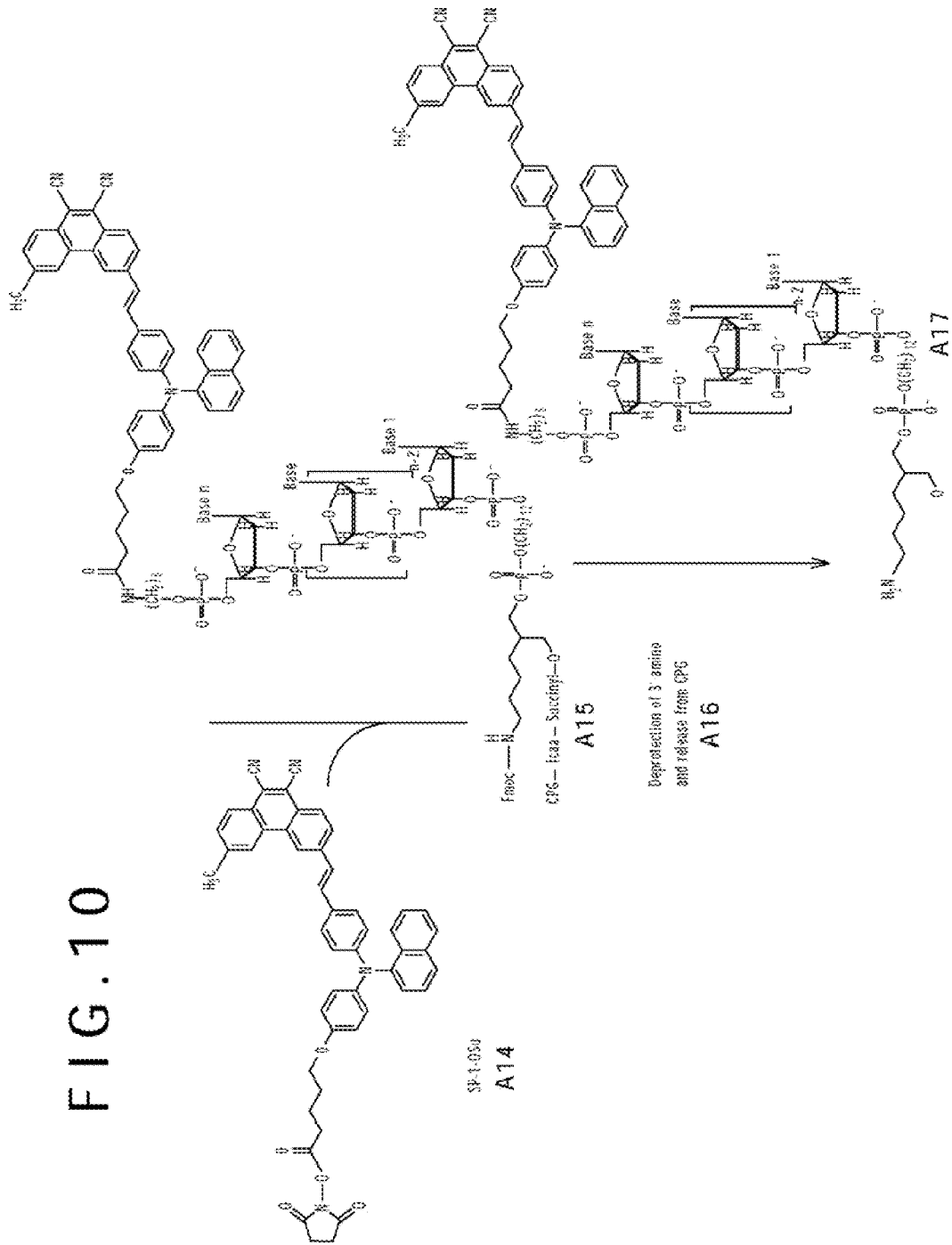
FIG. 10 is a view subsequent to the synthetic scheme of FIG. 9.

FIGS. 8, 9 and 10 are, respectively, a view showing an example of a synthetic scheme of an aromatic amine fluorescent probe embodying the invention and illustrate a synthetic scheme of a 3'-amino-5'-SP-1-oligonucleotide probe. FIG. 9 is a view subsequent to the synthetic scheme of FIG. 8 and FIG. 10 is a view subsequent to the synthetic scheme of FIG. 9.

The following reactions are generally carried out by use of a DNA solid phase synthetic apparatus.

Initially, as shown in FIG. 8, the procedure is started from reaction {A1+A2→A3}. A1 indicates a 3'-amino-modifier C7 CPG (see FIG. 14A), and A2 indicates a spacer phosphoramidite (Spacer C12 CE Phosphoramidite, made by Glen Research Corp.).

Next, reaction {A3+A4→A5} is carried out to permit the first nucleotide to be bound to A3. A4 (which is true of A6, A8 appearing hereinafter) indicates dN-CE phosphoramidite (made by Glen Research Corp.), and N=A, T, G or C. Subsequently, reaction {A5+A6→A7} is carried out thereby binding the second nucleotide to A5 in the same manner as set out above. Subsequently, a similar reaction {A7+A8→A9} is repeatedly carried out to permit binding nucleotides up to a desired nth nucleotide on the order of desired base species.

Next, reaction {A9+A10→A11} is carried out. A9 is 5'-amino-modifier C6 (see FIG. 14D). Subsequently, reaction {A11+A12→A13} is carried out to deprotect the 5'-amino to provide $NH_2$ at the 5' terminal. In a manner as stated above, there is formed, on the solid phase CPG, an oligonucleotide having a desired base sequence and terminated with $NH_2$ at the 5' terminal.

Figure 14A:
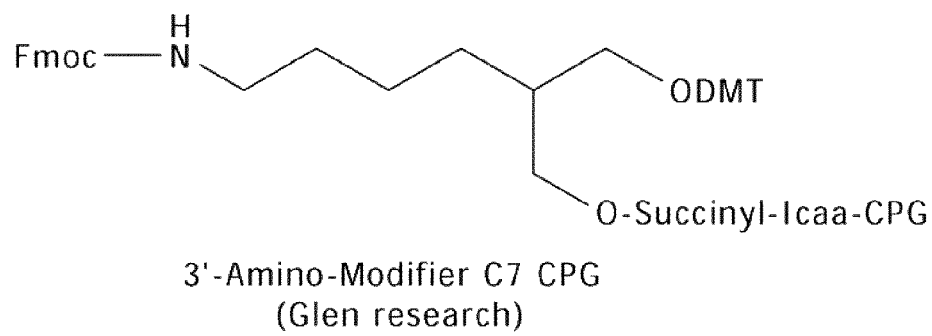
FIGS. 14A to 14D are examples of a solid phase support and reagents used in the synthesis of an oligonucleotide probe in an embodiment.
Figure 14B:
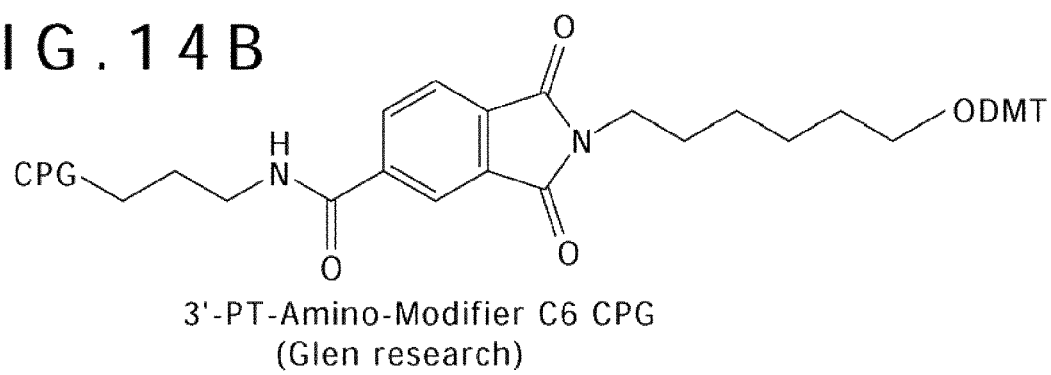
Figure 14C:
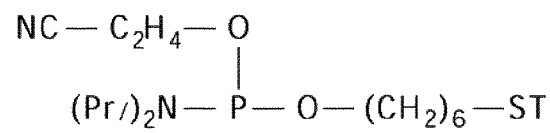
Figure 14D:
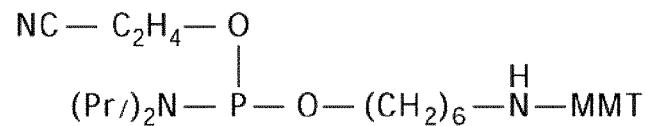
Figure 15:
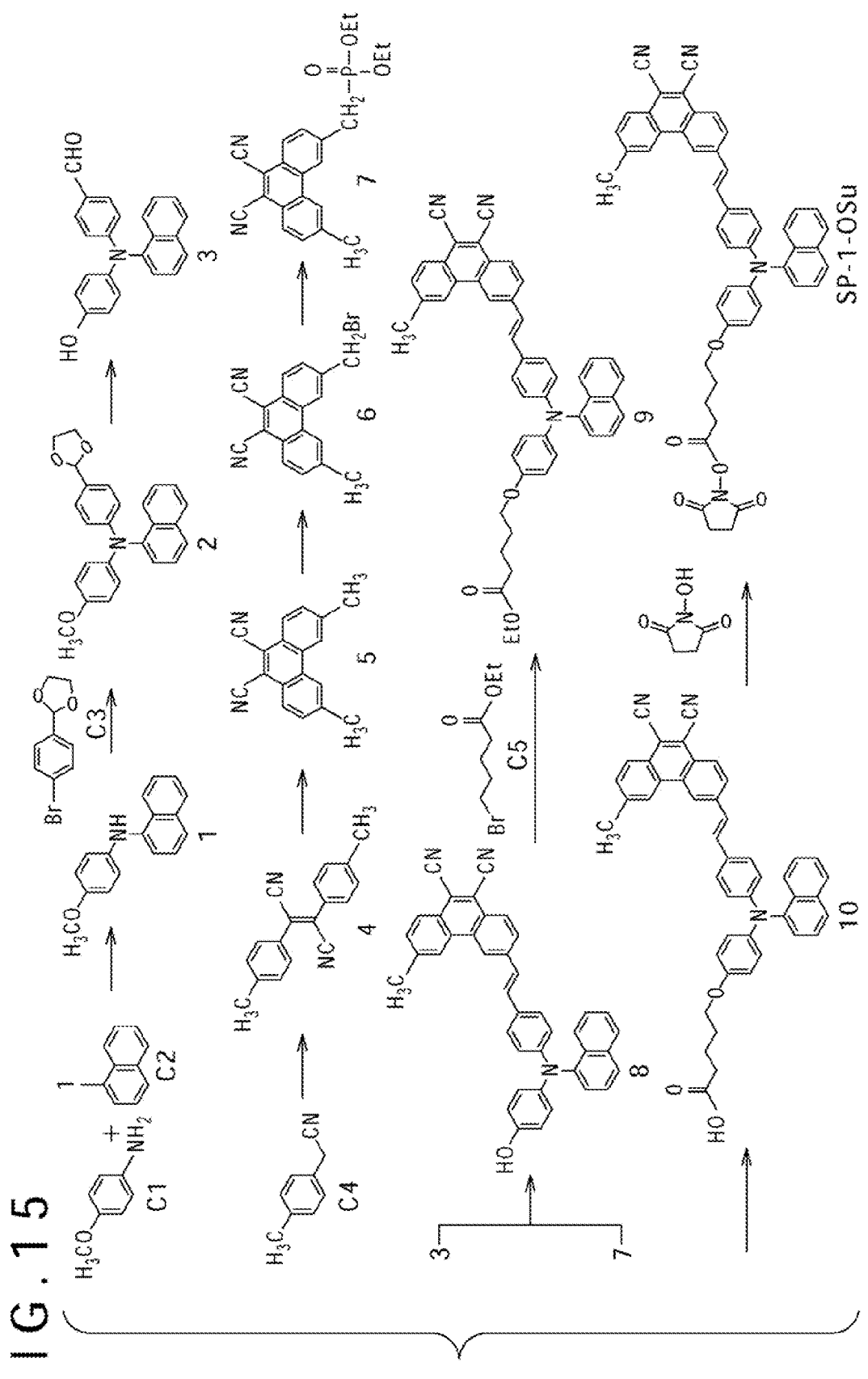
FIG. 15 is a view illustrating absorption and fluorescence spectra of an intermediate SP-1-OSu employed in the synthesis of an oligonucleotide probe in an example.

Next, reaction {A13+A14→A15} is carried out to bind A13 with SP-1-OSu (intermediate (activated esterified compound), see FIGS. 14 and 15). Subsequently, reaction {A15+A16→A17} is carried out to deprotect the 3' amino group and separate from CPG, thereby obtaining A17, i.e. a 3'-amino-5'-Sp1-oligonucleotide probe shown in FIG. 5 wherein SP-1 is bound to the 5' terminal and the 3' side is terminated with $NH_2$.

It will be noted that N-hydroxysuccinimide ($C_4H_5NO_3$) is represented by HOSu and —$C_4H_4NO_3$ is represented by -OSu herein and whenever they appear hereinafter in the ensuing figures.

It will also be noted that it may be possible to modify the 3'-amino-5'-SP-1-oligonucleotide probe at the 3' terminal by binding with a dye different in type from that bound at the 5' terminal, thereby obtaining an oligonucleotide probe modified with dyes that are different from each other at the 5' and 3' terminals. In doing so, there can be obtained, for example, a probe wherein an acceptor dye and a donor dye are bonded at given distance whereby fluorescence resonance energy transfer (FRET) occurs. This probe can be used for a variety of assays.

Figure 11:
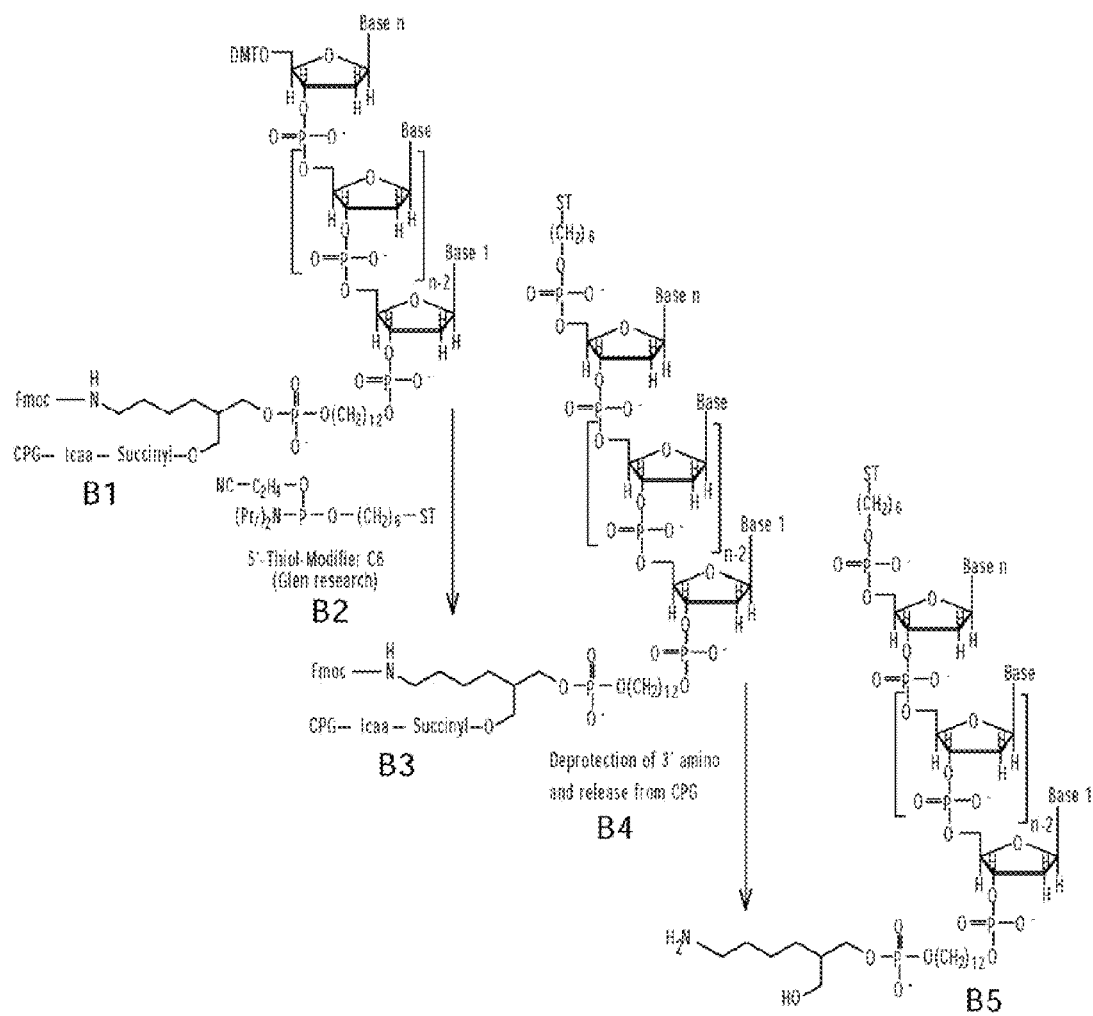
FIG. 11 is a view showing an example of a synthetic scheme of an aromatic amine fluorescent probe and particularly illustrating a synthetic scheme of 3'-BSA-2-5'-thio-oligonucleotide probe in an embodiment.
Figure 12:
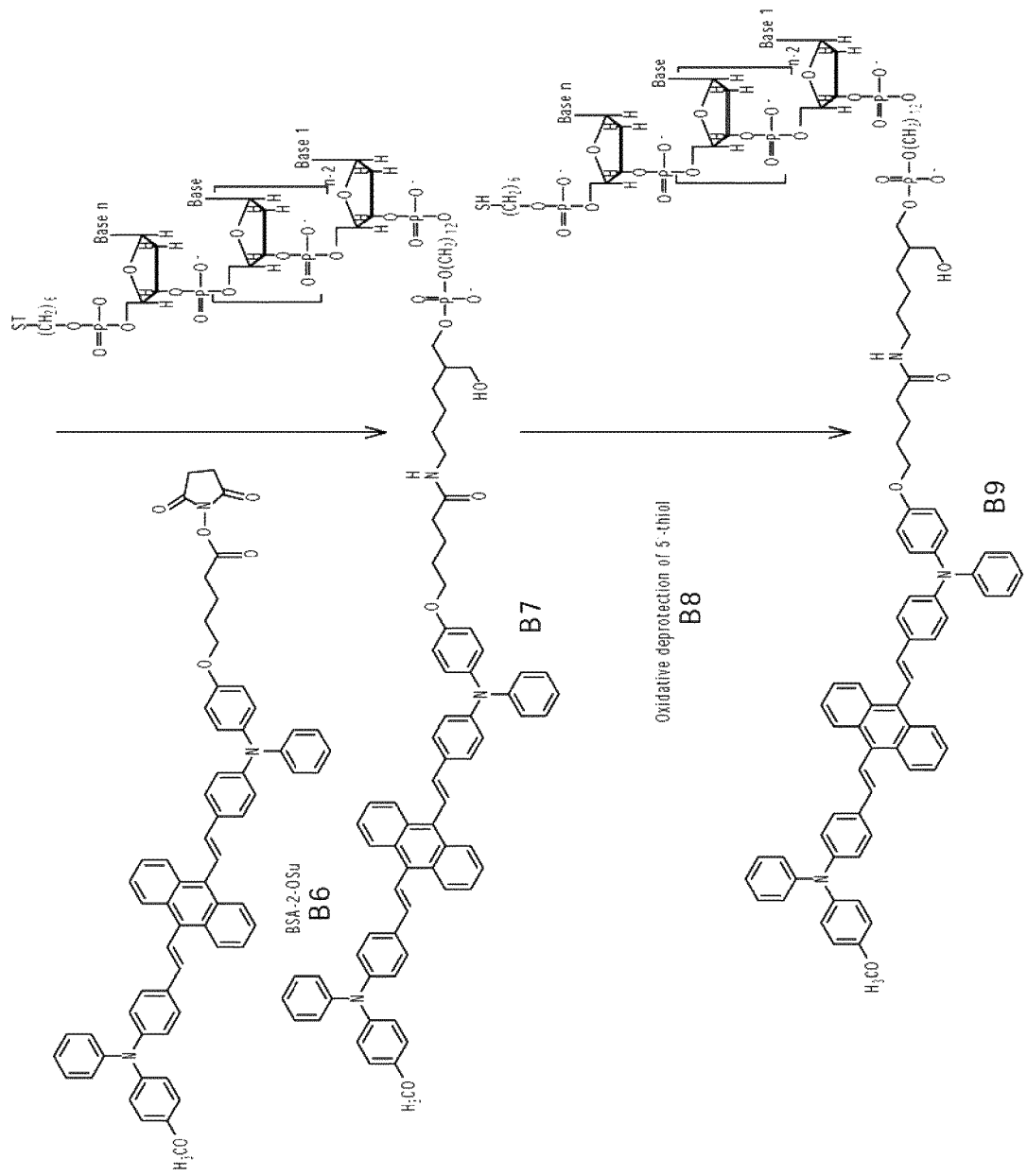
FIG. 12 is a view subsequent to the synthetic scheme of FIG. 11.

FIGS. 11 and 12 are a view showing an example of a synthetic scheme of an aromatic amine fluorescent probe according to an embodiment and illustrate a synthetic scheme of 3'-BSA-2-5'-thio-oligonucleotide probe. FIG. 12 shows the steps subsequent to the synthetic scheme of FIG. 11.

Initially, as shown in FIG. 11, reaction {B1+B2→B3} is carried out. B1 is same as A9 obtained in FIG. 8, and B2 is 5'-amino-modifier C6 (see FIG. 14C). Subsequently, reaction {B3+B4→B5} is carried out. The 3'-amino is deprotected and separated from CPG, thereby obtaining B5 wherein ST (T is a triphenylmethyl group) is bound to the 5' terminal and $NH_2$ is at the 3' terminal.

Thereafter, reaction {B5+B6→B7} is carried out. B6 is an intermediate (activated esterified compound) BSA-2-OSu which has been preliminarily prepared by reaction between aromatic amine compound BSA-2 (BSA-2 shown in FIG. 3 provided that $R^{47}$=$CH_3$) and HOSu (N-hydroxysuccinimide ($C_4H_5NO_3$)).

Next, reaction {B7+B8→B9} is carried out and the 5'-thiole is subjected to oxidative deprotection to obtain B9, i.e. 3'-BSA-2-5'-thio-oligonucleotide probe shown in FIG. 7, wherein the 5' terminal group is SH and BSA-2 is bound to the 3' terminal.

Examples of the solid phase support and reagent useful in FIGS. 8 to 12 are, respectively, those made by Glen Research Corporation and particularly shown in FIGS. 13A to 13D and also in FIGS. 14A to 14D.

FIGS. 13A to 13D illustrate examples of the solid phase support used in the synthesis of the oligonucleotide probes according to the invention.

As shown in FIGS. 13A to 13D, compounds required for the synthesis of an oligonucleotide are available in the form supported on a polystyrene microbead or CPG. When using the solid phase supports shown in FIGS. 13A and 13C, a nucleotide having an arbitrary one of A, T, G and C can be provided as the first nucleotide of an oligonucleotide.

When using the solid phase supports shown in FIGS. 13B and 13D, a nucleotide having a specified one of A, T, G and C can be provided as the first nucleotide of an oligonucleotide. It will be noted that in FIG. 13B, CPG to which Icaa is bound is not shown. It will also be noted that in FIGS. 13A to 13D, CPG (controlled porous glass) indicates a porous glass bead, Me indicates a methyl group, protected base means a base protected with a protective group, DMT indicates a dimethoxytrityl group, and Icaa indicates a long-chain alkylamino group.

FIGS. 14A to 14D illustrate examples of a solid phase support and a reagent used in the synthesis of oligonucleotide probes.

FIGS. 14A and 14B show examples of a solid phase support and the supports of FIGS. 14A and 14B are used for amino modification at 3' terminal side. FIGS. 14C and 14D show examples of a reagent, and the reagent of FIG. 14C is for thiole modification at the 5' terminal side and FIG. 14D is used for amino modification at the 5' terminal side. It will be noted that Fmoc indicates a 9-fluorenylmethoxy group, DMT indicates a dimethoxytrityl group, Icaa indicates a long-chain alkylamino group, CPG indicates a porous glass bead, Pri indicates an isopropyl group, ST indicates an S-trityl group, and MMT indicates a monomethoxytrityl group.

As stated hereinbefore, the oligonucleotide probe is synthesized through preparation of an oligonucleotide using a solid phase support, preparation of intermediate compounds such as BSA-2-OSu, SP-1-OSu and the like and binding reaction between the thus prepared two molecules.

Next, SP-1-OSu is taken as an example of an intermediate compound and the synthetic process and the results thereof are illustrated, and synthesis of 3'-amino-5'-SP-1-oligonucleotide probe is described.

EXAMPLES

Synthesis of Intermediate SP-1-OSu

FIG. 15 is a view illustrating an intermediate SP-1-OSu used for the synthesis of an oligonucleotide probe (i.e. 3'-amino-5'-SP-1-oligonucleotide probe) in an example of the invention.

(1) Synthesis of Compound 1

A suspension, in 500 ml of dehydrated xylene, of 505 g (4.12 mols) of p-anisidine (C1 (in FIG. 15), p-methoxyaniline ($CH_3OC_6H_4NH_2$)), 105 g of (0.41 mols) of 1-iodonaphthalene (C2 (in FIG. 15), 1-iodonaphthalene ($C_{10}H_7I$)), 1.85 g (8.24 mmols) of $Pd(OAc)_2$ (palladium (II) diacetate (Pd(O-$COCH_3)_2$), 5.00 g (24.7 mmols) of tri-tert-butylphosphine $P(C(CH_3)_3)$, and 47.5 g (0.49 mols) of sodium tert-butoxide ($C_4H_9ONa$) was gently refluxed for 21 hours in an atmosphere of argon. After cooling, hydrochloric acid was added, followed by extraction with ethyl acetate. The organic phase was washed with dilute hydrochloric acid and dried over anhydrous magnesium sulfate, followed by drying under reduced pressure. The resulting concentrated residue was purified with a silica gel column (toluene) and the resulting crude product was washed with methanol to obtain 68.9 g (yield of 66%) of colorless compound 1.

(2) Synthesis of Compound 2

A suspension, in 78 ml of dehydrated xylene, of 19.6 g (78.6 mmols) of the compound 1, 19.7 g (86.4 mmols) of 2-(4-bromophenyl)-1,3-dioxorane (C3 in FIG. 15, $C_9H_9BrO_2$), 0.35 g (1.57 mmols) of $Pd(OAc)_2$, 0.95 g (4.7 mmols) of tri-tert-butylphosphine and 9.06 g (94.3 mols) of sodium tert-butoxide was gently refluxed for 19 hours in an atmosphere of argon. After cooling, water was poured, followed by extraction with toluene. The resulting organic phase was washed with water and dried over anhydrous magnesium sulfate, followed by concentration under reduced pressure. The concentrate residue was purified with a silica gel column (toluene) to obtain 25.2 g (yield of 80%) of yellow viscous liquid compound 2.

(3) Synthesis of Compound 3

A mixed solution of 14.5 g (36.5 mmols) of compound 2 and 145 g of 30% HBr—HOAc (acetic acid ($CH_3COOH$)) was refluxed for 3 hours. After cooling, water and methylene chloride were added to the solution, followed by separation of the insoluble matter by filtration. The filtrate was separated and the organic phase was washed with water and dried over anhydrous magnesium sulfate, followed by concentration under reduced pressure. The concentrate residue was purified with a silica gel column (methylene chloride-ethyl acetate/hexane=½) to obtain 3.71 g (yield of 30%) of yellow amorphous compound 3.

(4) Synthesis of Compound 4

97.1 g (0.38 mols) of iodine was added to 760 ml of a dehydrated ether solution of 50.2 g (0.38 mols) of p-xylyl cyanide (C4 in FIG. 15, $C_{10}H_8N_2$), in which 148 g (0.77 mols, 28% in MeOH) of sodium methoxide ($CH_3ONa$) was dropped over 15 minutes while cooling with water. After stirring at room temperature for 30 minutes, the solvent was distilled off under reduced pressure. The resulting concentrated residue was washed with methanol several times to obtain 40.5 g (yield of 82%) of deep green crystalline compound 4.

(5) Synthesis of Compound 5

4.5 liters of a toluene solution of 15.0 g (58.1 mmols) of the compound 4 was irradiated with a high pressure mercury lamp, under which the solution was stirred for 7 hours while bubbling with oxygen. The reaction mixture was concentrated under reduced pressure and the resulting slurry precipitation was filtered. The resulting crude product was washed with toluene to obtain 13.3 g (yield of 89%) of light bright yellow crystalline compound 5.

(6) Synthesis of Compound 6

22.9 g (129 mmols) of NBS (2-nitrobenzenesulfenyl chloride ($C_6H_4NO_2SCl$) and 1.05 g (6.45 mmols) of AIBN (azo-bisisobutyronitrile ($NCC(CH_3)_2NN(CH_3)CCN$)) were, respectively, added to 858 ml of a chloroform solution of 11.0 g (42.9 mmols) of the compound 5 by ⅕ of the total amount in every 3 hours, followed by refluxing for 15 hours in total. The resulting solution was concentrated under reduced pressure and the slurry precipitation was filtered. The resulting crude product was washed with ethanol and hexane to obtain 14.1 g of a mixture containing light brown crystalline compound 6.

(7) Synthesis of Compound 7

A mixture of 13.5 g of the mixture containing compound 6 and 40.5 g of triethylphosphite (triethoxy phosphine ($P(OC_2H_5)_3$) was stirred for 24 hours at 145° C. Excess triethyl phosphite was distilled off under reduced pressure and washed with hexane. The resulting residue was purified with a silica gel column (methylene chloride—THF/methylene chloride=⅛) to obtain 6.58 g of bright yellow crystal compound 7. The two-step yield from compound 5 was 39%.

(8) Synthesis of Compound 8

0.64 g (15.9 mmols) of 60% oily sodium hydride (NaH) was subjected to oil removal in an atmosphere of argon, to which 100 ml of dehydrated THF and 2.19 g (5.57 mmols) of compound 7 were added. After stirring for 10 minutes at room temperature, 50 ml of a dehydrated THF solution of 1.80 g (5.30 mmols) of compound 3 was dropped at 0° C. or below in 20 minutes. After stirring for 4 hours at the same temperature, excess sodium hydride was quenched with ethanol and subsequently with water, and the resulting organic phase was washed with a saline solution and dried over anhydrous magnesium sulfate, followed by concentration under reduced pressure. The resulting concentrated residue was washed with methanol several times to obtain 2.68 g (yield of 87%) of red crystalline compound 8.

(9) Synthesis of Compound 9

0.150 g (3.74 mmols) of 60% oily sodium hydride was subjected to oil removal in an atmosphere of argon, to which 25 ml of dehydrated DMF (dimethylformamide, $(CH_3)_2NCHO$), in which 100 ml of a dehydrated THF solution of 0.90 g (1.56 mmols) of compound 8 was dropped under stirring. 1.95 g of ethyl bromopentanoate (C5 (FIG. 15), $CH_2Br(CH_2)_3COOC_2H_5$) was added and stirred at room temperature for 30 minutes, followed by stirring at 65° C. for 15 hours. Excess sodium hydride was quenched with ethanol and subsequently with water, and the resulting organic phase was dissolved in toluene, washed with water and dried over anhydrous magnesium sulfate, followed by concentration under reduced pressure. The resulting concentrated residue was washed with methanol several times to obtain 1.06 g (yield of 96%) of orange crystalline compound 9.

(10) Synthesis of Compound 10

A 10% sodium hydroxide aqueous solution (4.16 mmols) was added to 20 ml of a THF solution of 0.98 g (1.39 mmols) of compound 9 and stirred for 1 hour at 50° C. Further, 20 ml of THF, 4 ml of ethanol and a 10% sodium hydroxide aqueous solution (11.1 mmols) were added to the solution and stirred for 3 hours at 60° C. Precipitated crystals were separated by filtration and washed with THF. THF and hydrochloric acid were added to the resulting solid for dissolution, followed by removal of an insoluble material by filtration. The filtrate was concentrated under reduced pressure to obtain 0.69 g (yield of 73%) of dark brown crystalline compound 10. This compound 10 is a tertiary amine compound SP-1 (more accurately, an aromatic tertiary amine compound prior to binding with the molecular chain oligo (oligonucleotide) in the fluorescent probe SP-1 shown in FIG. 2).

(11) Synthesis of SP-1-OSu 0.43 g (2.04 mmols) of N,N'-dicyclohexylcarbodiimide (DCC, $C(NC_6H_{11})_2$) and 0.24 g (2.04 mmols) of N-hydroxysuccinimide (HOSu, $C_4H_5NO_3$) were added to 20 ml of a THF solution of 0.69 g (1.02 mmols) of compound 10, and stirred at room temperature for 16 hours. The solvent was removed under reduced pressure, and methanol was added for washing to the resulting concentrated residue to obtain 0.70 g (yield of 88% and purity of 97.2% when determined by HPLC (high performance liquid chromatography)) of SP-1-OSu in the form of red crystals.

As stated hereinabove, the intermediate SP-1-OSu can be synthesized according to reaction {(tertiary amine compound SP-1)+HOSu→SP-1-OSu+$H_2O$}. More accurately, in the fluorescent probe SP-1 shown in FIG. 2, when the tertiary amine compound prior to binding with the molecular chain oligo (oligonucleotide) is taken as Dy-OH, the intermediate compound Dy-OSu can be synthesized according to reaction {(Dy-OH)+HOSu→Dy-OSu+$H_2O$}.

B6 used in FIG. 12, i.e. BSA-2-OSu, can be synthesized in the same manner as with the synthesis of SP-1-OSu by reaction between an amine compound BSA-2 (BSA-2 shown in FIG. 3 provided that $R^{47}$=$CH_3$) and HOSu (N-hydroxysuccinimide).

In the fluorescent probes shown in FIGS. 2, 3 and 4, when the aromatic tertiary amine compound prior to binding with the molecular chain oligo (oligonucleotide) is indicated as Dy-OR and R is —H or an alkyl group, e.g. —$CH_3$, the intermediate compound Dy-OSu can be synthesized according to reaction {(Dy-OR)+HOSu→Dy-OSu+ROH}.

FIG. 16 is a $^1$H-NMR (nuclear magnetic resonance) spectral chart of the intermediate SP-1-OSu prepared in the example of the invention.

In FIG. 16, the horizontal axis indicates a chemical shift (ppm) and the vertical axis indicates a nuclear magnetic resonance signal intensity. The chemical shift values at the respective signal peaks are indicated above the peaks, and signal integration is indicated in the vicinity of the signal peaks. It will be noted that NMR spectra were measured by use of NMR instrument, Model Number JNM-AL400 FT, made by JEOL Ltd.

δppm (400 MHz, CDCl$_3$): 1.98(m, 4H), 2.71(m, 5H), 2.84 (m, 2H), 3.98(m, 2H), 6.84(m, 4H), 7.14-7.49(m, 10H), 7.65 (d, 1H), 7.79(d, 1H), 7.89-8.00(m, 3H), 8.72-8.29(m, 2H), 8.54(s, 1H), 8.62(s, 1H)

15 aliphatic hydrogen atoms are observed at 1.9 to 4.0 ppm and 23 aromatic hydrogen atoms are observed at 6.8 to 8.6 ppm, which is supporting the molecular structure of SP-1-OSu.

Figure 17:
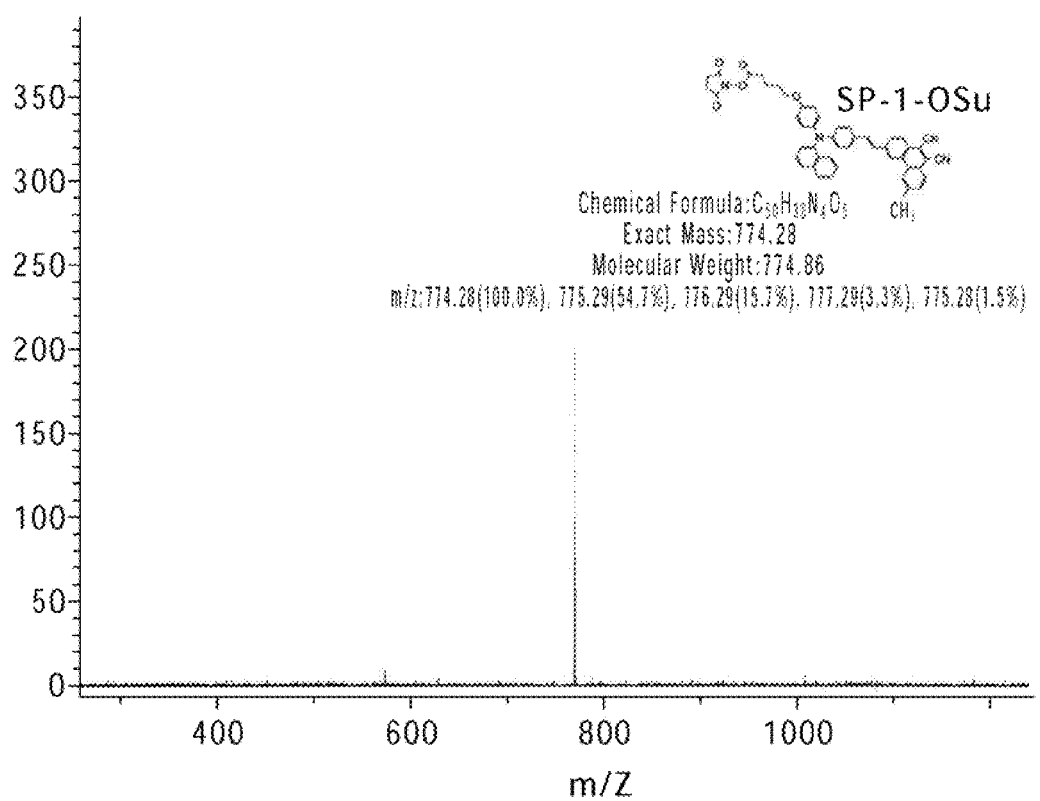
FIG. 17 is a chart of MS spectra of the synthesized intermediate SP-1-OSu in the example.

FIG. 17 is an MS spectral chart of intermediate SP-1-OSu prepared in the example.

The MS spectra shown in FIG. 17 are ones that are measured by use of MALDI-TOF-MS (matrix assisted laser desorption ionization-time of flight-mass spectrometer) and the instrument used for the measurement was Model KRATOS AMA/IA-CFR, made by Shimadzu Corporation.

As shown in FIG. 17, the molecular weight of intermediate SP-1-OSu (chemical formula: $C_{50}H_{38}N_4O_5$) calculated is at 774.27, whereas the molecular weight determined from m/z related to the respective measured peaks (wherein m=molecular weight and z=number of charges) and a pattern coefficient (coefficient of appearance rate) was at 774.86.

The NMR spectra and MS spectra shown in FIGS. 16 and 17 give evidence that the synthesized intermediate compound SP-1-OSu is just as desired.

<Absorption and Emission Characteristics of Intermediate Compound SP-1-OSu>

The absorption and emission characteristics of the synthesized intermediate compound SP-1-OSu are illustrated. The absorption spectra and emission spectra were, respectively, measured by use of spectrophotometer Model U-3310 and fluorophotometer Model FL-4500, both made by Hitachi Ltd.

Figure 18A:
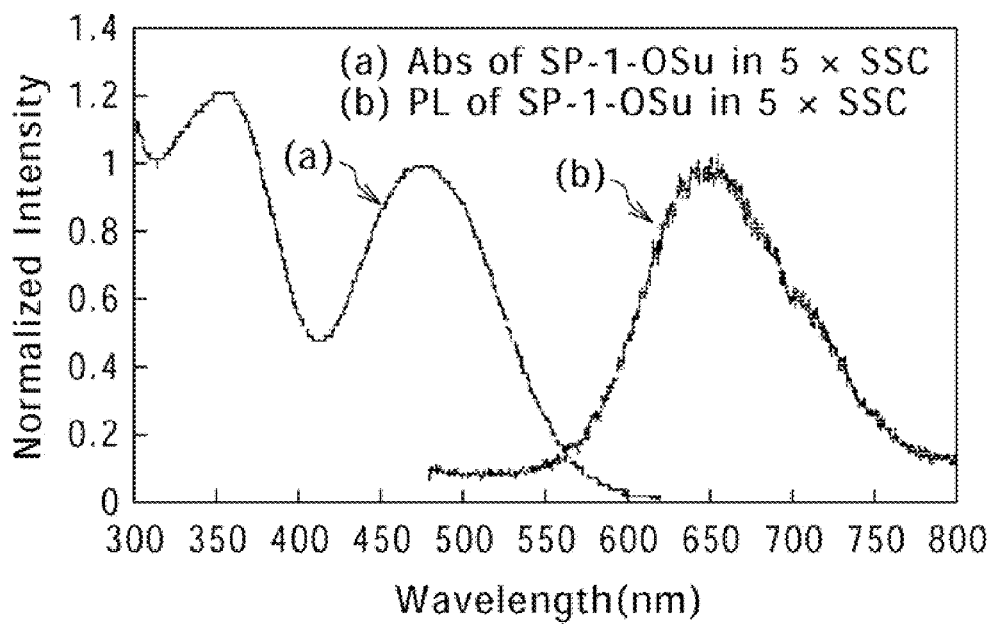
FIGS. 18A and 18B are charts of absorption and fluorescence spectra of the synthesized intermediate SP-1-OSu in the example.
Figure 18B:
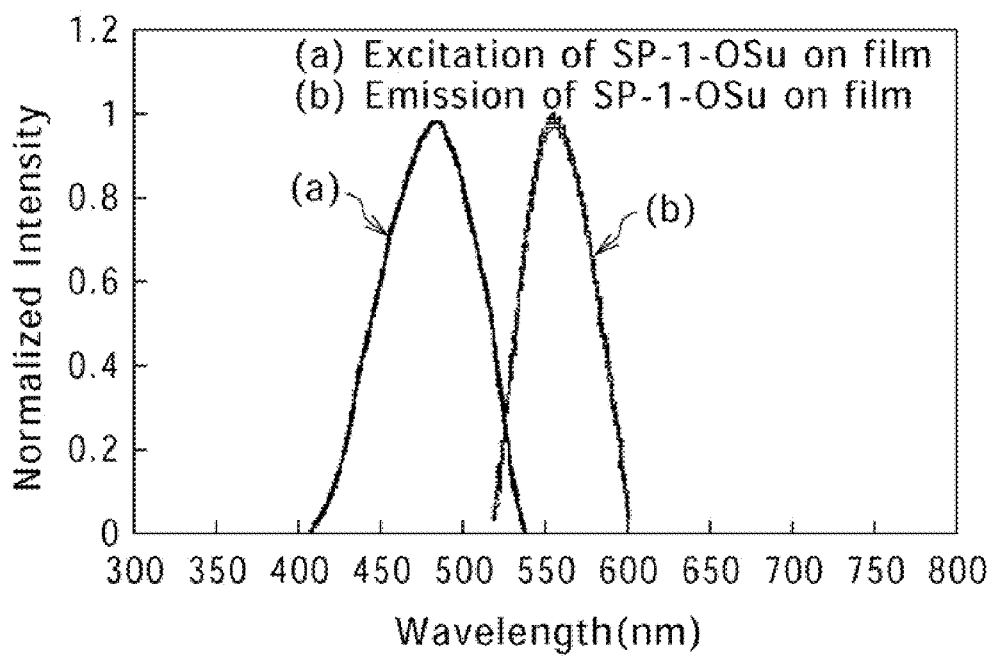

FIGS. 18A and 18B are absorption and fluorescence spectral charts of intermediate SP-1-OSu under different measuring conditions, respectively, wherein FIG. 18A is a spectral chart in the state of a solution and FIG. 18B is a spectral chart in a dried state.

In FIGS. 18A and 18B, the horizontal axis indicates a wavelength (nm) and the vertical axis indicates a relative intensity in case where maximal values of absorption and fluorescence spectra are normalized, taken as 1.0.

Initially, the absorption spectra ((a) in FIG. 18A) and fluorescence spectra ((b) in FIG. 18A) of the intermediate SP-1-OSu in the form of a solution are illustrated.

The absorption maximum of a solution of the intermediate SP-1-OSu in a 10% EtOH:5×SSC buffer used as a solvent was at 474 nm with a molar absorption coefficient being at 120,000 $M^{-1}$ $cm^{-1}$. The fluorescent maximum was at 650 nm and the fluorescence yield was at 0.0081. The Stokes shift obtained from the peaks of the absorption and fluorescence spectra was at 176 nm. It will be noted that the fluorescence yield was determined by measurement of a relative fluorescence yield wherein using Rhodamine 101 (having an absolute fluorescence yield of 0.96) as a reference substance, and a relative fluorescence yield was calculated according to the following equation $$QY_f(s)/QY_f(r)=[Area(s)/Abs(s)]/[Area(r)/Abs(r)]$$

Wherein
$QY_f(s)$=relative fluorescence yield of a sample,
$QY_f(r)$=absolute fluorescence yield of a reference substance, a value in literature,
Area(s)=fluorescence spectral area of a sample,
Area(r)=fluorescence spectral area of a reference substance,
Abs(s)=absorbance of a sample, and
Abs(r)=absorbance of a reference substance.

Next, the absorption spectra ((a) in FIG. 18B) and the fluorescence spectra ((b) in FIG. 18B) of the intermediate SP-1-OSu in dried state are described.

An epoxy resin SU-8 (SU-8-3035-N-02, made by Kayaku Microchem Co., Ltd.) was diluted to 50% by use of cyclopentanone and spin coated (first at 500 rpm for 15 second and second at 1500 rpm for 30 seconds) onto an ozone-treated glass substrate, followed by drying at 100° C. for 2 minutes. The epoxy resin was photocured by UV irradiation with a 50 mW/cm² xenon lamp for 6 seconds and annealed at 150° C. for 10 minutes. The epoxy resin-bearing substrate was heated along with 3-aminopropyltriethoxysilane in an oven of 120° C. and the amino group was introduced into the substrate. SP-1-OSu was dissolved in DMF at a concentration of 10 mM, in which the amino group-bearing substrate was immersed for 2 hours to cause the SP-1-OSu to be supported on the substrate. The excitation peak of the SP-1-OSu layer on the substrate in dry state was at 484 nm. The emission peak was at 556 nm. The Stokes shift calculated from the peaks of the absorption and fluorescence spectra was 72 nm.

As stated above, the intermediate SP-1-OSu exhibited large Stokes shifts in either a solution or a dry state. Such a dye enables us to design an excitation filter, which has an optically-transparent wavelength region fitting an absorption peak of the dye but not overlapping with the fluorescent spectrum of it. And thus, it maximizes the excitation efficiency. Likewise, the dye enables us to design an emission filter, which has an optically-transparent wavelength region fitting a fluorescent peak of the dye but not overlapping with the absorption spectrum of it. And thus, it maximizes the fluorescent intensity. More particularly, the optically-transparent wavelength region of the excitation filter and the optically-transparent wavelength region of the fluorescent filter can be significantly separated from each other, and thus, it becomes easy to cut off stray light from emission of sample.

Figure 19A:
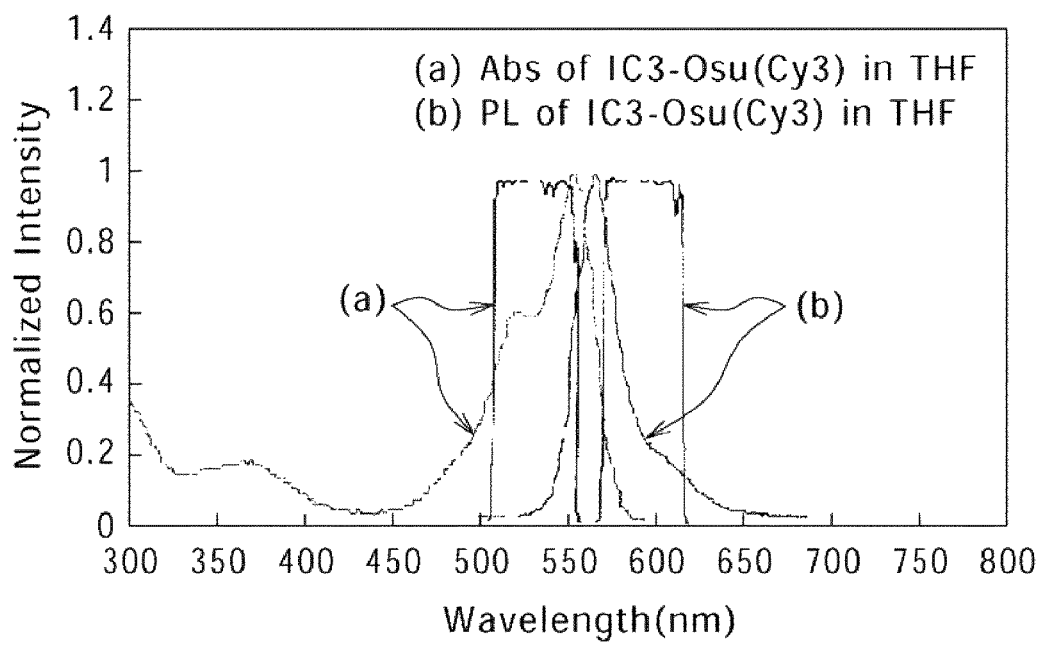
FIGS. 19A and 19B are charts of absorption and fluorescence spectra for comparison.
Figure 19B:
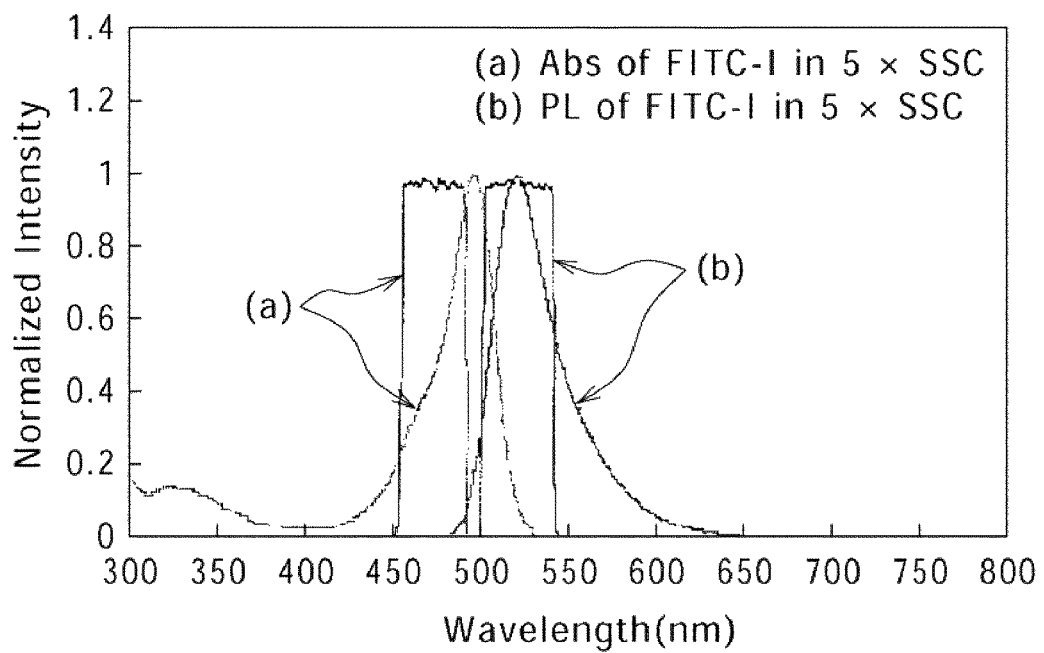

FIGS. 19A and 19B are individually an absorption and fluorescence spectral chart for comparison wherein FIG. 19A is a spectral chart relating to IC3-OSu (Cy3) measured in a 5×SSC buffer and FIG. 19B is a spectral chart relating to FITC-I measured in a THF solution.

In FIGS. 19A and 19B, (a) indicates an excitation spectrum and an excitation filter and (b) indicates a fluorescence spectrum and a fluorescence filter. With the examples shown in FIGS. 19A and 19B, the excitation filter and fluorescence filter have such wavelength transmission regions that are so close to each other. The transmittance data of the excitation filter and fluorescence filter are those laid open by Semrock Co., Ltd.

IC3-OSu (Cy3) is a labeling agent of Dojindo Laboratories and is similar to Cy3, made by GE Healthcare Bioscience KK. FITC-I is one wherein an isothiocyanate group is bound to fluorescein.

Formula (a): Molecular Structure of IC3-OSu

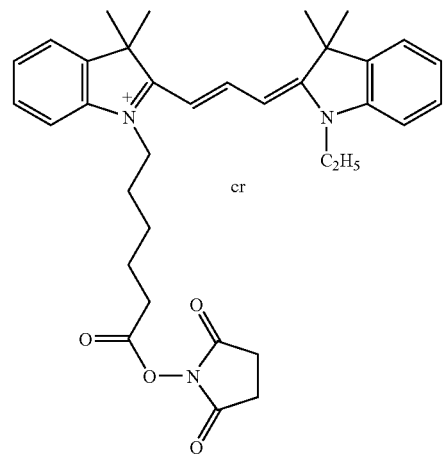

Formula (b): Molecular Structure of FITC-I

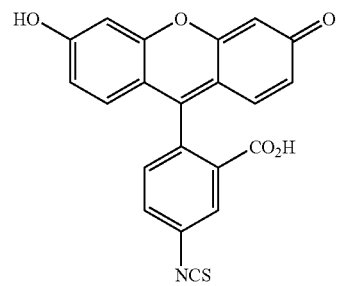

As shown in FIG. 19A, IC3-OSu has a Stokes shift of about 10 nm and as shown in FIG. 19B, FITC-I has a Stokes shift of about 25 nm.

As will be apparent from the comparison between FIGS. 18A and 18B and 19A and 19B, the intermediate SP-1-OSu has a Stokes shift much greater than those of IC3-OSu and FITC-I either in dry state or in solution.

It will be noted that when the respective dye solutions of SP-1 were kept in a glass container and allowed to stand under irradiation of a fluorescent lamp, it was confirmed that Cy3 lost its color in one month, and SP-1 underwent no change and was excellent in light resistance.

Cy3 and derivatives of fluorescein readily suffer degradation, for example, by application of a laser or a high-power light source, making reproducible repeated measurements difficult. In this connection, however, SP-1 does not undergo such degradation and is usable in reproducible, repeated measurements.

Next, the relation between the molecular structure of a dye and the spectrum and the difference in photooxidation resistance are described based on the results of the study using molecular orbital calculation.

The dye Cy3 having two olefinic (ethylenic) double bonds and represented by the molecular formula $C_{25}H_{26}N_2Cl$ (i.e. a dye of the above-mentioned formula (a) wherein the $N^+$—$C_{10}H_{14}O_4N$ portion is changed to N—$CH_3$ and the $NC_2H_5$ portion is changed to N—$CH_3$) and the dye SP represented by the molecular formula $C_{42}H_{29}N_3$ (i.e. a dye of the chemical formula 8 indicated in FIG. 15 having a structure wherein —OH is changed to —$CH_3$) have been checked.

The dye Cy3 and dye SP were, respectively, according to the molecular orbital calculation, subjected to structural optimization of the ground state and energy levels of HOMO (highest occupied molecular orbital) and LUMO (lowest occupied molecular orbital) in the ground state were determined. Next, one electron was removed from HOMO of the ground state, then it was put onto LUMO with spin-flipping. After the structural re-optimization in which modified LUMO was regarded as the initial excited state, the energy levels of HOMO and LUMO were calculated. In addition, structural changes in the ground and excited states were checked.

With the dye Cy3, the energy levels of HOMO in the ground state and LUMO in the excited state calculated according to the molecular orbital calculation were, respectively, at 6.26 eV and 2.56 eV, and the Stokes shift which is a gap between those levels was at 3.7 eV.

With the dye SP, the energy levels of HOMO in the ground state and LUMO in the excited state calculated according to the molecular orbital calculation were, respectively, at 7.22 eV and 2.39 eV, and the Stokes shift was at 4.83 eV. Hence, the Stokes shift of the dye SP is greater than the Stokes shift of the dye Cy3.

With the dye Cy3, the nature of HOMO and LUMO is, respectively, attributed to the II electronic conjugation of the central olefinic double bond, and the structural change associated with excitation, i.e. the structural change in the ground and excited states, is small. Since there is only a small difference in the envelope-shaped electric cloud between two states, both the structural change and Stokes shift are small in the case of Cy3.

With HOMO of the dye Cy3, electrons are localized at the olefinic double bond site and the electron density of the olefinic double bond is so high that the dye is liable to undergo electrophilic attack such like oxidization by oxygen.

The structural change of the dye SP associated with excitation, or the structural change in the ground and excited states, is observed: (1) in the difference of a twisted angle around the olefinic (ethylenic) double bond connecting the phenanthrene ring and the phenyl ring as viewed from the upper face of the phenanthrene ring, (2) in the difference of an angle around the amine nitrogen (N) as viewed from the axial direction of the above-mentioned olefinic double bond, (3) in the difference of an angle between the planes, respectively, made by the phenanthrene ring and the phenyl ring (a ring located between the amine nitrogen (N) and the olefinic double bond) and the difference in planarity of the phenanthrene ring, i.e. a difference in positional relation of the plane made by the phenanthrene relative to the plane made by the phenyl ring.

In the dye SP, electrons are localized at the electron-donative amine site for HOMO and electrons are localized at the electron-attractive phenanthrene site for LUMO. The transition from the ground state to the exited state is of the charge-transfer type and the electron density of the olefinic double bond is small. As a result of the difference in the electron density between HOMO and LUMO, such structural differences as set out in (2) and (3) above are caused.

With the dye SP, electrons move from the amine site toward the phenanthrene site through excitation and the olefinic double bond is greatly twisted to cause the structural change. Thus, the difference between the structure in the excited state and the structure in the ground state becomes great, resulting in a great Stokes shift. Since the electron density of the olefinic double bond is small, the electrophilic reaction is unlikely to occur and the dye is unlikely to be oxidized by the attack of oxygen.

The labeled compound according to the invention has one or two amine moiety (e.g. an amine moiety where a phenyl ring or a naphthyl ring is bound to amine nitrogen, or an electro-donating site) bound to a cyano-arene (e.g. an phenanthrene ring substituted with cyano group(s), or an electro-withdrawing site) through the olefinic (ethylenic) double bond of the styryl moiety. As the large polarization occurs in the molecule, red shift occurs both in the absorption and the fluorescence.

In order to detect the longer-wavelength fluorescence at high sensitivity, it is applicable to use photomultiplier tube (PMT) whose detection sensitivity in region longer than 500 nm is improved, e.g. PMT using GaAsP as a photocathode.

As set forth hereinabove, the labeled compound of the invention is larger in Stokes shift and higher in light resistance than existing labeled compounds. Accordingly, the optically-transparent wavelength region of an excitation filter and an optically-transparent wavelength region of a fluorescence filter can be satisfactorily separated from each other. Therefore, a fluorescence emitted from a sample can be separated from other unnecessary stray light and the like. A sample molecule can be detected at high sensitivity and at a high SN ratio. The compound is excellent in light resistance, for which if an intensity of excitation light is increased for detection of trace amounts of molecules, a data variation due to photodegradation of a labeled compound is scarcely experienced. Thus, stable repetitions of measurement are possible and reproducibility of repeated measurements can be improved.

<Synthesis of a 3'-amino-5'-SP-1-oligonucleotide Probe>

The afore-indicated intermediate SP-1-OSu (A14) and an oligonucleotide (the number of bases n=30) (A13) synthesized by use of a DNA solid phase synthesizer were reacted according to the scheme shown in FIGS. 9 and 10, and the 3'-amino group was deprotected to prepare 3'-amino-5'-SP-1-oligonucleotide probe (A17).

The results of the synthesis of the 3'-amino-5'-SP-1-oligonucleotide probe were confirmed by use of HPLC, Model MALDI-TOF-MS, with respect to the purity and structure thereof.

It will be noted that the intermediate SP-1-OSu is the compound used in the synthetic scheme (see FIGS. 8 to 10) of the 3'-amino-5'-SP-1-oligonucleotide probe. This intermediate SP-1-O-Su may be used as a compound capable of covalent bonding with a biomolecule, i.e. a fluorescently-labeled compound.

It will also be noted that the intermediate SP-1-OSu is an ester having an active-esterified carbonyl group (an N-hydroxysuccinimide ester group (called an NHS group or an OSu group)), which covalently binds with an amino group of an amino acid or protein. Accordingly, the intermediate SP-1-OSu can be used as a fluorescently-labeled compound.

For instance, SP-1-OSu is bound to a biomolecule having an amino group such as of an amino acid or a protein and is thus labeled, and allows a fluorescence to be generated through photoexcitation. Thus, a biomolecule can be detected and the intermediate can be used as a fluorescent labeling compound for biomolecules.

For instance, the labeled compound can be bound to an antigen molecule, a ligand molecule and a sugar protein, respectively, and an antibody molecule, a receptor molecule and a lectin molecule bound to the former molecules, respectively, can be detected.

Thus, the embodiments provide a labeled compound capable of detecting a living body-derived molecule at high sensitivity at a high SN ratio.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A labeled compound designed to enable an aromatic tertiary amine compound represented by the following general formula (1) to be bound with a sample molecule:

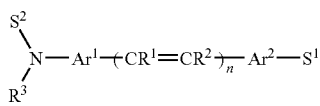

in which n is 0 or 1, one of $S^1$ and $S^2$ represents a first group in which a molecular chain capable of binding with a sample molecule is bound directly or indirectly to a divalent spacer having an alkyl chain that may have a divalent group selected from the following Gp1, or a reactive group selected from the following Gp3, the other of $S^1$ and $S^2$ represents a group selected from the following Gp2, $Ar^1$ is a phenylene group, $Ar^2$ is one of a phenylene group, a naphthylene group, a phenanthrene group and an anthrylene group, and $R^1$ and $R^2$ are individually a hydro group, and the general formula (1) is re-formulated as the following general formula (2):

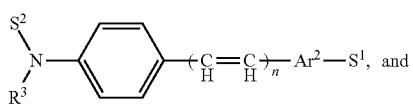

$R^3$ represents a group selected from a hydro group, an alkyl group that may have a substituent selected from the following Gp2, an aryl group that may have a substituent group, and a vinyl group that may have a substituent group, provided that Gp1 is a divalent group and represents an arylene group that may contain a hetero atom, a vinylene group, a carbonyl group, an oxy group, an oxycarbonyl group, a thio group, a sulfinyl group, a sulfonyl group, an imino group, a urylene group, an amide group or a silylene group, Gp2 is a monovalent group and represents a hydro group, an alkyl group, an aryl group, a vinyl group that may contain a substituent group, an amino group, a mercapto group, a hydroxy group, a carbamoyl group, a sulfino group, a sulfo group, a carboxy group or a halo group, and Gp3 is a monovalent group and represents an N-hydroxysuccinimide ester group, a hydroxysulfosuccinimide ester group, an imide ester group, an isothiocyanate group, an isocyanate group, a maleimide group, a carboxyl group, an aldehyde group, a glyoxal group, an imido ester group, an oxirane group, a triazine group, a carbodiimide group, an aziridine group, a halogenated acyl group, a halogenated alkyl group, a halogenated sulfonyl group or a vinyl sulfone group, and wherein said molecular chain is made of an oligonucleotide.

2. The labeled compound according to claim 1, wherein $S^2$ is said first group.

3. The labeled compound according to claim 1, wherein $S^2$ is said first group and $S^1$ is a 4-aminostyryl group, and said general formula (1) is re-formulated as the following general formula (3):

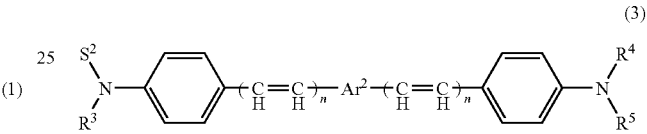

in which $R^4$ and $R^5$ may be the same or different and a group selected from a hydro group, an alkyl group which may have a substituent group and an aryl group which may have a substituent group.

4. The labeled compound according to claim 1, wherein $S^2$ is said first group, which contains a phenyl group substituted with $R^6$, $R^7$, $R^8$, $R^9$ and $R^{10}$ provided that said spacer is bound through said Gp1 to one of $R^6$, $R^7$, $R^8$, $R^9$ and $R^{10}$, said molecular chain is bound through said Gp1 to said spacer and the others of $R^6$, $R^7$, $R^8$, $R^9$ and $R^{10}$ individually represent a hydro group, and $R^3$ is an aryl group containing a phenyl group substituted with $R^{11}$, $R^{12}$, $R^{13}$, $R^{14}$ and $R^{15}$, in which $R^{11}$, $R^{12}$, $R^{13}$, $R^{14}$ and $R^{15}$ individually represent a group selected from said Gp2 provided that adjacent groups among the groups may join together to from a ring, and said general formula (2) is re-formulated as the following general formula (4):

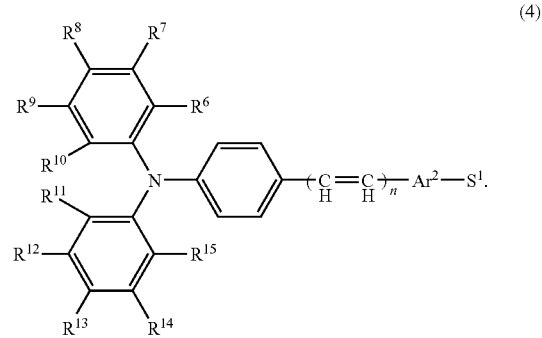

5. The labeled compound according to claim 3, wherein $S^2$ represents said first group, which contains a phenyl group substituted with $R^6$, $R^7$, $R^8$, $R^9$ and $R^{10}$ provided that said spacer is bound through said Gp1 to any one of $R^6$, $R^7$, $R^8$, $R^9$ and $R^{10}$, said molecular chain is bound through said Gp1 to said spacer, and the others of $R^6$, $R^7$, $R^8$, $R^9$ and $R^{10}$ individually represent a hydro group, $R^3$ represents an aryl group containing a phenyl group substituted with $R^{11}$, $R^{12}$, $R^{13}$, $R^{14}$, and $R^{15}$ provided that $R^{11}$, $R^{12}$, $R^{13}$, $R^{14}$ and $R^{15}$ are individually a group selected from the Gp2 and adjacent ones may join together to form a ring, $R^4$ represents an aryl group having a phenyl group substituted with $R^{16}$, $R^{17}$, $R^{18}$, $R^{19}$ and $R^{20}$, and $R^5$ is an aryl group having a phenyl group substituted with $R^{21}$, $R^{22}$, $R^{23}$, $R^{24}$ and $R^{25}$ wherein $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ individually represent a group selected from said Gp2 and adjacent groups among the groups may link together to form a ring, and said general formula (3) is re-formulated as the following general formula (5):

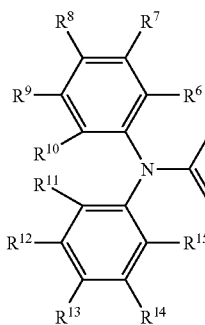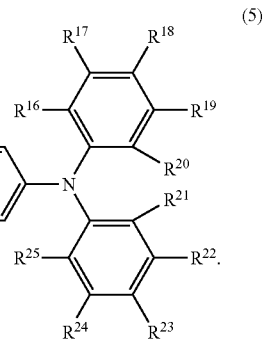

(5)

6. The labeled compound according to claim 1, wherein $S^1$ is said first group.

7. The labeled compound according to claim 6, wherein $S^2$ is an aryl group having a phenyl group substituted with $R^{26}$, $R^{27}$, $R^{28}$, $R^{29}$ and $R^{30}$, $R^3$ is an aryl group having a phenyl group substituted with $R^{31}$, $R^{32}$, $R^{33}$, $R^{34}$ and $R^{35}$, and $R^{26}$, $R^{27}$, $R^{28}$, $R^{29}$, $R^{30}$, $R^{31}$, $R^{32}$, $R^{33}$, $R^{34}$ and $R^{35}$ individually represent a group selected from those of Gp2 provided that adjacent groups among the groups may join together to form a ring, and said general formula (3) is re-formulated as the following general formula (6):

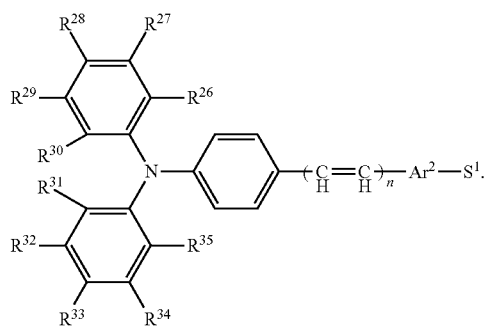

(6)

8. The labeled compound according to claim 1, wherein said alkyl chain has not less than 3 to not more than 20 carbon atoms.

9. The labeled compound according to claim 1, wherein said sample molecule is a living body-derived molecule.

10. The labeled compound according to claim 1, wherein said oligonucleotide has a length of from not less than 5 mer to not more than 40 mer.

11. The labeled compound according to claim 1, wherein said oligonucleotide is used as a probe for detecting a complementary oligonucleotide strand of said living body-derived molecule having a complementary strand sequence thereof.

12. The labeled compound according to claim 1, wherein $R^3$ is a phenyl group or a naphthyl group.

13. The labeled compound according to claim 1, wherein $Ar^1$—$(CR^1$=$CR^2)_n$—$Ar^2$ in which n is 0 or 1 in the general formula (1) includes repeating units of C=C— and has N—(C=C—)$_m$ in which m≧6 when the number of the repeating units is taken as m.

14. A detection method of a sample molecule using a labeled compound, the method comprising the steps of:
  binding a labeled compound defined in a labeled compound designed to enable an aromatic tertiary amine compound represented by the following general formula (1) to be bound with a sample molecule

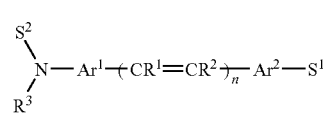

(1)

in which n is 0 or 1,
  one of $S^1$ and $S^2$ represents a first group wherein a molecular chain capable of binding with a sample molecule is bound directly or indirectly to a divalent spacer having an alkyl chain that may have a divalent group selected from the following Gp1, or a reactive group selected from the following Gp3, the other of $S^1$ and $S^2$ represents a group selected from the following Gp2,
  $Ar^1$ is a phenylene group, $Ar^2$ is one of a phenylene group, a naphthylene group, a phenanthrene group and an anthrylene group, and $R^1$ and $R^2$ are individually a hydro group, and the general formula (1) is re-formulated as the following general formula (2):

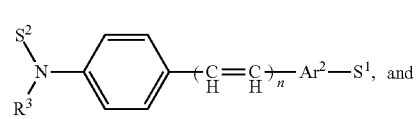

(2)

, and $R^3$ represents a group selected from a hydro group, an alkyl group that may have a substituent selected from the following Gp2, an aryl group that may have a substituent group and a vinyl group that may have a substituent group, provided that Gp1 is a divalent group and represents an arylene group that may contain a hetero atom, a vinylene group, a carbonyl group, an oxy group, an oxycarbonyl group, a thio group, a sulfinyl group, a sulfonyl group, an imino group, a urylene group, an amide group or a silylene group, Gp2 is a monovalent group and represents a hydro group, an alkyl group, an aryl group, a vinyl group that may contain a substituent group, an amino group, a mercapto group, a hydroxy group, a carbamoyl group, a sulfino group, a sulfo group, a carboxy group or a halo group, and Gp3 is a monovalent group and represents an N-hydroxysuccinimide ester group, a hydroxysulfosuccinimide ester group, an imide ester group, an isothiocyanate group, an isocyanate group, a maleimide group, a carboxyl group, an aldehyde group, a glyoxal group, an imido ester group, an oxirane group, a triazine group, a carbodiimide group, an aziridine group, a halogenated acyl group, a halogenated alkyl group, a halogenated sulfonyl group or a vinyl sulfone group, to a sample molecule; and detecting a fluorescence emitted from said labeled compound bound to said sample molecule by irradiation of light, wherein said molecular chain is made of an oligonucleotide.

15. A labeled compound designed to enable an aromatic tertiary amine compound represented by the following general formula (1) to be bound with a sample molecule:

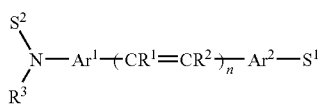

(1)

in which n is 0 or 1, one of $S^1$ and $S^2$ represents a first group in which a molecular chain capable of binding with a sample molecule is bound directly or indirectly to a divalent spacer having an alkyl chain that may have a divalent group selected from the following Gp1, or a reactive group selected from the following Gp3, the other of $S^1$ and $S^2$ represents a group selected from the following Gp2, $Ar^1$ is a phenylene group, $Ar^2$ is one of a phenylene group, a naphthylene group, a phenanthrene group and an anthrylene group, and $R^1$ and $R^2$ are individually a hydro group, and the general formula (1) is re-formulated as the following general formula (2):

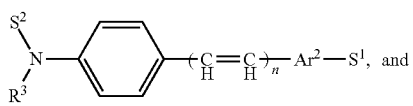

(2)

$R^3$ represents a group selected from a hydro group, an alkyl group that may have a substituent selected from the following Gp2, an aryl group that may have a substituent group, and a vinyl group that may have a substituent group, provided that Gp1 is a divalent group and represents an arylene group that may contain a hetero atom, a vinylene group, a carbonyl group, an oxy group, an oxycarbonyl group, a thio group, a sulfinyl group, a sulfonyl group, an imino group, a urylene group, an amide group or a silylene group, Gp2 is a monovalent group and represents a hydro group, an alkyl group, an aryl group, a vinyl group that may contain a substituent group, an amino group, a mercapto group, a hydroxy group, a carbamoyl group, a sulfino group, a sulfo group, a carboxy group or a halo group, and Gp3 is a monovalent group and represents an N-hydroxysuccinimide ester group, which binds with an amino group contained in said sample molecule.

16. A detection method of a sample molecule using a labeled compound, the method comprising the steps of:

binding a labeled compound defined in a labeled compound designed to enable an aromatic tertiary amine compound represented by the following general formula (1) to be bound with a sample molecule

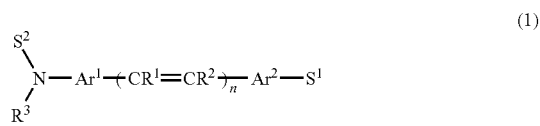

(1)

in which n is 0 or 1, one of $S^1$ and $S^2$ represents a first group wherein a molecular chain capable of binding with a sample molecule is bound directly or indirectly to a divalent spacer having an alkyl chain that may have a divalent group selected from the following Gp1, or a reactive group selected from the following Gp3, the other of $S^1$ and $S^2$ represents a group selected from the following Gp2, $Ar^1$ is a phenylene group, $Ar^2$ is one of a phenylene group, a naphthylene group, a phenanthrene group and an anthrlenegro and $R^1$ and $R^2$ are individually a hydro group, and the general formula (1) is re-formulated as the following general formula (2):

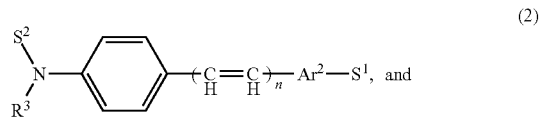

(2)

$R^3$ represents a group selected from a hydro group, an alkyl group that may have a substituent selected from the following Gp2, an aryl group that may have a substituent group and a vinyl group that may have a substituent group, provided that Gp1 is a divalent group and represents an arylene group that may contain a hetero atom, a vinylene group, a carbonyl group, an oxy group, an oxycarbonyl group, a thio group, a sulfinyl group, a sulfonyl group, an imino group, a urylene group, an amide group or a silylene group, Gp2 is a monovalent group and represents a hydro group, an alkyl group, an aryl group, a vinyl group that may contain a substituent group, an amino group, a mercapto group, a hydroxy group, a carbamoyl group, a sulfino group, a sulfo group, a carboxy group or a halo group, and Gp3 is a monovalent group and represents an N-hydroxysuccinimide ester group, which binds with an amino group contained in said sample molecule; and detecting a fluorescence emitted from said labeled compound bound to said sample molecule by irradiation of light.

17. A labeled compound designed to enable an aromatic tertiary amine compound represented by the following general formula (1) to be bound with a sample molecule:

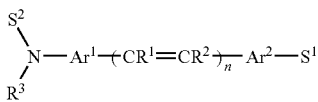
(1)

in which n is 0 or 1,
one of $S^1$ and $S^2$ represents a first group in which a molecular chain capable of binding with a sample molecule is bound directly or indirectly to a divalent spacer having an alkyl chain that may have a divalent group selected from the following Gp1, or a reactive group selected from the following Gp3, the other of $S^1$ and $S^2$ represents a group selected from the following Gp2,
$Ar^1$ is a phenylene group, $Ar^2$ is one of a phenylene group, a naphthylene group, a phenanthrene group and an anthrylene group, and $R^1$ and $R^2$ are individually a hydro group, and the general formula (1) is re-formulated as the following general formula (2):

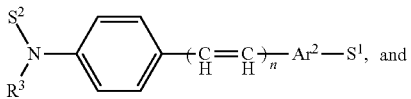
(2)

$R^3$ represents a group selected from a hydro group, an alkyl group that may have a substituent selected from the following Gp2, an aryl group that may have a substituent group, and a vinyl group that may have a substituent group, provided that
Gp1 is a divalent group and represents an arylene group that may contain a hetero atom, a vinylene group, a carbonyl group, an oxy group, an oxycarbonyl group, a thio group, a sulfinyl group, a sulfonyl group, an imino group, a urylene group, an amide group or a silylene group,
Gp2 is a monovalent group and represents a hydro group, an alkyl group, an aryl group, a vinyl group that may contain a substituent group, an amino group, a mercapto group, a hydroxy group, a carbamoyl group, a sulfino group, a sulfo group, a carboxy group or a halo group, and
Gp3 is a monovalent group and represents a maleimide group, which binds with a mercapto group contained in said sample molecule.

18. A detection method of a sample molecule using a labeled compound, the method comprising the steps of:

binding a labeled compound defined in a labeled compound designed to enable an aromatic tertiary amine compound represented by the following general formula (1) to be bound with a sample molecule

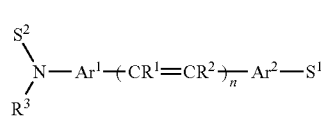
(1)

in which n is 0 or 1,
one of $S^1$ and $S^2$ represents a first group wherein a molecular chain capable of binding with a sample molecule is bound directly or indirectly to a divalent spacer having an alkyl chain that may have a divalent group selected from the following Gp1, or a reactive group selected from the following Gp3, the other of $S^1$ and $S^2$ represents a group selected from the following Gp2,
$Ar^1$ is a phenylene group, $Ar^2$ is one of a phenylene group, a naphthylene group, a phenanthrene group and an anthrylene group, and $R^1$ and $R^2$ are individually a hydro group, and the general formula (1) is re-formulated as the following general formula (2):

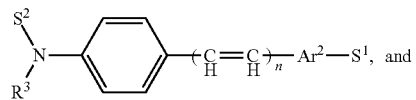
(2)

$R^3$ represents a group selected from a hydro group, an alkyl group that may have a substituent selected from the following Gp2, an aryl group that may have a substituent group and a vinyl group that may have a substituent group, provided that
Gp1 is a divalent group and represents an arylene group that may contain a hetero atom, a vinylene group, a carbonyl group, an oxy group, an oxycarbonyl group, a thio group, a sulfinyl group, a sulfonyl group, an imino group, a urylene group, an amide group or a silylene group,
Gp2 is a monovalent group and represents a hydro group, an alkyl group, an aryl group, a vinyl group that may contain a substituent group, an amino group, a mercapto group, a hydroxy group, a carbamoyl group, a sulfino group, a sulfo group, a carboxy group or a halo group, and
Gp3 is a monovalent group and represents a maleimide group, which binds with a mercapto group contained in said sample molecule; and
detecting a fluorescence emitted from said labeled compound bound to said sample molecule by irradiation of light.

* * * * *